(12) United States Patent
Shimokawatoko et al.

(10) Patent No.: US 9,000,219 B2
(45) Date of Patent: Apr. 7, 2015

(54) METHOD FOR TREATMENT OF ISOCYANATE RESIDUE, AND METHOD FOR TREATMENT OF CARBONATE

(75) Inventors: Yoshiki Shimokawatoko, Chiba (JP); Koichi Murayama, Chiba (JP); Hiroshi Takeuchi, Ichihara (JP); Takashi Kanno, Ichihara (JP); Masaaki Sasaki, Ichihara (JP); Kazuhiko Okubo, Minato-ku (JP)

(73) Assignee: Mitsui Chemicals, Inc., Tokyo (JP)

( * ) Notice: Subject to any disclaimer, the term of this patent is extended or adjusted under 35 U.S.C. 154(b) by 50 days.

(21) Appl. No.: 13/517,005

(22) PCT Filed: Dec. 14, 2010

(86) PCT No.: PCT/JP2010/072431
§ 371 (c)(1),
(2), (4) Date: Jun. 18, 2012

(87) PCT Pub. No.: WO2011/078000
PCT Pub. Date: Jun. 30, 2011

(65) Prior Publication Data
US 2012/0271067 A1 Oct. 25, 2012

(30) Foreign Application Priority Data

Dec. 24, 2009 (JP) ................................ 2009-293387
May 11, 2010 (JP) ................................ 2010-109623
May 11, 2010 (JP) ................................ 2010-109624

(51) Int. Cl.
*C07C 211/00* (2006.01)
*C07C 263/04* (2006.01)
*C07C 29/12* (2006.01)
(Continued)

(52) U.S. Cl.
CPC ............... *C07C 263/04* (2013.01); *C07C 29/12* (2013.01); *C07C 209/62* (2013.01); *C07C 269/04* (2013.01)

(58) Field of Classification Search
None
See application file for complete search history.

(56) References Cited

U.S. PATENT DOCUMENTS 4,501,915 A * 2/1985 McCoy ........................ 560/157
5,386,053 A 1/1995 Otterbach et al.
(Continued)

FOREIGN PATENT DOCUMENTS

CN 101084179 A 12/2007
DE 2421503 * 11/1974
(Continued)

OTHER PUBLICATIONS

Derwent Abstract of DE 2421503.*
(Continued)

*Primary Examiner* — Karl J Puttlitz
(74) *Attorney, Agent, or Firm* — Foley & Lardner LLP

(57) ABSTRACT

A method for treating an isocyanate residue, which comprises carrying out a thermal decomposition reaction of a carbamate that is produced by the reaction among an amine, urea and/or an N-unsubstituted carbamic acid ester and an alcohol to produce a decomposition solution, separating an isocyanate and the alcohol from the decomposition solution to produce the isocyanate residue, and bringing the isocyanate residue into contact with high-pressure/high-temperature water to decompose the isocyanate residue into an amine; and a method for treating a carbonate, which comprises bringing the carbonate into contact with high-pressure/high-temperature water to decompose the carbonate into an alcohol.

7 Claims, 3 Drawing Sheets

(51) Int. Cl.
*C07C 209/62* (2006.01)
*C07C 269/04* (2006.01)

(56) References Cited

U.S. PATENT DOCUMENTS

| | | | | |
|---|---|---|---|---|
| 5,449,817 | A * | 9/1995 | Jensen | 560/345 |
| 6,255,529 | B1 * | 7/2001 | Nagase et al. | 564/414 |
| 6,462,230 | B1 | 10/2002 | Nagase et al. | |
| 7,875,253 | B2 * | 1/2011 | Yoshida et al. | 422/187 |
| 2003/0012710 | A1 | 1/2003 | Nishida et al. | |
| 2005/0250960 | A1 | 11/2005 | Kohlstruk et al. | |
| 2009/0275776 | A1 | 11/2009 | Kasuya et al. | |
| 2011/0190534 | A1 | 8/2011 | Kasuya et al. | |

FOREIGN PATENT DOCUMENTS

| | | |
|---|---|---|
| EP | 0 976 719 A1 | 2/2000 |
| EP | 1 903 026 A1 | 3/2008 |
| JP | 6-25136 | 2/1994 |
| JP | 9-151270 | 6/1997 |
| JP | 10-279539 | 10/1998 |
| JP | 2005-320334 | 11/2005 |
| JP | 2006069941 * | 3/2006 |
| JP | 2008-195646 | 8/2008 |
| WO | WO-2005/102986 A2 | 11/2005 |

OTHER PUBLICATIONS

European Communication for Application No. EP 10 83 9233.3 dated Sep. 19, 2013, including Supplementary European Search Report, 6 pages.

International Search Report PCT/JP2010/072431 dated Mar. 22, 2011.

* cited by examiner

METHOD FOR TREATMENT OF ISOCYANATE RESIDUE, AND METHOD FOR TREATMENT OF CARBONATE

TECHNICAL FIELD

The present invention relates to a method for treating isocyanate residues, and more particularly, to a method for treating isocyanate residues obtained as residual substances in production of isocyanates which are raw materials for polyurethane or the like.

The present invention relates to a method for treating carbonates, and more particularly, to a method for treating carbonates such as dialkyl carbonate, diaryl carbonate, or alkyl aryl carbonate.

BACKGROUND ART

The isocyanate is a compound having at least one isocyanate group (—NCO) and is industrially widely used as a raw material for polyurethane or polyurea.

Conventionally, isocyanates are industrially produced by reaction between amine and phosgene (phosgene method). There are, however, various disadvantages such that phosgene is hard to deal with due to its highly toxic nature and also by-produces hydrochloric acid in large quantity, so that corrosion of systems needs to be considered. Accordingly, it is desirable to develop an alternative method for industrially producing isocyanates.

As a method for producing isocyanates without using phosgene, for example, a method (carbonate method) of forming amines into carbamates using dialkyl carbonate and then thermally decomposing the obtained carbamates; and a method (urea method) of forming amines into carbamates using urea or N-unsubstituted carbamic acid ester and then thermally decomposing the obtained carbamates are known.

According to these methods, it is possible to produce carbamates without using phosgene and then decompose them into isocyanate and alcohol.

More specifically, there has been proposed, for example, a method for producing isocyanates and alcohol, which includes allowing organic polyamines, urea, and alcohols to react in the presence of dialkyl carbonates and alkyl carbamates to give polyurethanes (carbamates), removing the alcohol, the dialkyl carbonates, and the alkyl carbamates from the reaction mixture containing the obtained polyurethanes (carbamates), and then recycling the resultants into the reaction step of organic polyamines, urea, and alcohols, and thermally decomposing the reaction mixture containing the obtained polyurethanes (carbamates) (see, for example, the following Patent Document 1).

According to this method, polyurethanes (carbamates) are obtained as main products by allowing organic polyamines, urea, and alcohols to react, and simultaneously, dialkyl carbonates and alkyl carbamates obtained as by-products are recycled into the reaction step of organic polyamines, urea, and alcohols, so that the dialkyl carbonates and the organic polyamines are allowed to react, to thereby separately produce polyurethanes (carbamates).

The polyurethanes (carbamates) thus produced are thermally decomposed to thereby produce isocyanates without using phosgene.

It is, however, known for the carbonate method or the urea method that the carbamates or isocyanates produced, or intermediates thereof cause unpreferable polymerization reaction such as multimerization, biuretization, or allophanatization.

In this case, when the isocyanates and the alcohols are separated and recovered from the decomposition solution of carbamates, for example, by-products such as urea derivatives (biuret derivatives) or carbamate derivatives (allophanate derivatives) are obtained as isocyanate residues.

Although the phosgene method allows isocyanates to be produced by reaction between amine and phosgene, the isocyanates cause unpreferable polymerization reaction such as multimerization with this method, resulting in by-production of multimers or the like as isocyanate residues.

Such isocyanate residues are usually disposed of. In recent years, however, it is required that wastes should be reduced from the viewpoints of global environment and related factors, so that various methods for effectively using recovered isocyanate residues are studied. As one of such methods, there has been proposed, for example, a method for continuously feeding residues, which are by-produced when an isocyanate compound is produced by phosgene method, in a molten state or a solution state to a reactor as well as continuously feeding high-pressure/high-temperature water to the reactor, and setting the temperature in the reactor to 190 to 300° C., so that the residues are decomposed into polyamines to be recovered (see, for example, the following Patent Document 2).

In addition, carbonates such as dialkyl carbonate, diaryl carbonate, and alkyl aryl carbonate are used as various industrial materials, and they are known as by-products obtained when carbamates are produced by industrially allowing amine, urea and/or N-unsubstituted carbamic acid ester, and alcohol to react (carbamate formation reaction) as described above.

CITATION LIST

Patent Documents

Patent Document 1: Japanese Unexamined Patent Publication No. 6-25136
Patent Document 2: Japanese Unexamined Patent Publication No. 10-279539

DISCLOSURE OF THE INVENTION

Problems to be Solved

According to the method described in the above Patent Document 2, although the isocyanate residues by-produced in the phosgene method can be decomposed into amine, there is no disclosure of being able to decompose the isocyanate residues (e.g., urea derivatives, carbamate derivatives, etc.) which are not by-produced in the phosgene method but are by-produced in the carbonate method or urea method. These isocyanate residues are usually disposed of, but their effective use is still desired.

In the reaction given in the above Patent Document 1, the carbonates such as dialkyl carbonates obtained as by-products exhibit extremely low reactivity to amine as compared with urea or N-unsubstituted carbamic acid esters. Therefore, even if the dialkyl carbonates are recycled as described in Patent Document 1, it is difficult to industrially produce polyurethanes (carbamates) with efficiency.

From the industrial view point, it is desirable to effectively use various carbonates containing these by-products.

The object of the present invention is to provide a method for treating isocyanate residues, which includes decomposing isocyanate residues obtained from a decomposition solution of carbamates, into amine.

Another object of the present invention is to provide a method for treating carbonates to efficiently use the carbonates.

Means for Solving the Problem

The method for treating isocyanate residues according to the present invention comprises decomposing isocyanate residues which are obtained by separating isocyanate and alcohol from a decomposition solution resulting from thermal decomposition reaction of carbamate produced by reaction of amine, urea and/or N-unsubstituted carbamic acid ester, and alcohol, into amine by contact with high pressure and high temperature water.

In the method for treating isocyanate residues according to the present invention, it is preferable that the isocyanate residues are brought into contact with high pressure and high temperature water in the presence of a solvent.

In the method for treating isocyanate residues according to the present invention, it is preferable that carbonate is blended with the isocyanate residues and the isocyanate residues blended with the carbonate are brought into contact with high pressure and high temperature water.

In the method for treating isocyanate residues according to the present invention, it is preferable that the amine used for production of carbamate is an amine obtained by decomposing isocyanate residues, and the alcohol used for production of carbamate is an alcohol separated from the decomposition solution resulting from thermal decomposition reaction of carbamate.

In the method for treating isocyanate residues according to the present invention, it is preferable that the solvent is an aromatic hydrocarbon having a boiling point of 250° C. or higher.

In the method for treating isocyanate residues according to the present invention, it is preferable that after the isocyanate residues are decomposed, a solvent is recovered, and carbamate is thermally decomposed in the presence of the solvent recovered after the isocyanate residues are decomposed.

In the method for treating isocyanate residues according to the present invention, it is preferable that the carbonate is obtained by carbamate formation reaction of amine, urea and/or N-unsubstituted carbamic acid ester, and alcohol.

In the method for treating isocyanate residues according to the present invention, it is preferable that the carbonate is obtained by further roughly separating from low-boiling components containing carbonate separated after the carbamate formation reaction.

In the method for treating isocyanate residues according to the present invention, it is preferable that the carbonate contains N-unsubstituted carbamic acid ester.

In the method for treating isocyanate residues according to the present invention, it is preferable that the low-boiling components further contain N-unsubstituted carbamic acid ester, the carbonate as well as the N-unsubstituted carbamic acid ester is roughly separated from the low-boiling components, and the N-unsubstituted carbamic acid ester is used as a raw material component for the carbamate formation reaction.

The method for treating carbonates according to the present invention comprises decomposing at least one carbonate selected from the group consisting of dialkyl carbonate, diaryl carbonate, and alkyl aryl carbonate into alcohol by contact with high pressure and high temperature water.

In the method for treating carbonates according to the present invention, it is preferable that the carbonate is obtained by carbamate formation reaction of amine, urea and/or N-unsubstituted carbamic acid ester, and alcohol.

In the method for treating carbonates according to the present invention, it is preferable that the carbonate is obtained by further roughly separating from low-boiling components containing N-unsubstituted carbamic acid ester and carbonate, which are separated after the carbamate formation reaction.

In the method for treating carbonates according to the present invention, it is preferable that the carbonate contains N-unsubstituted carbamic acid ester.

In the method for treating carbonates according to the present invention, it is preferable that the alcohol obtained by decomposing the carbonate is used as a raw material component for the carbamate formation reaction.

In the method for treating carbonates according to the present invention, it is preferable that the N-unsubstituted carbamic acid ester is roughly separated from the low-boiling components and then used as a raw material component for the carbamate formation reaction.

Effect of the Invention

According to the method for treating isocyanate residues of the present invention, the isocyanate residues obtained from the decomposition solution of carbamates can be decomposed into amine.

According to the method for treating carbonates of the present invention, the carbonate can be decomposed into alcohol, so that the carbonate can be industrially effectively used.

EMBODIMENT OF THE INVENTION

Figure 1:
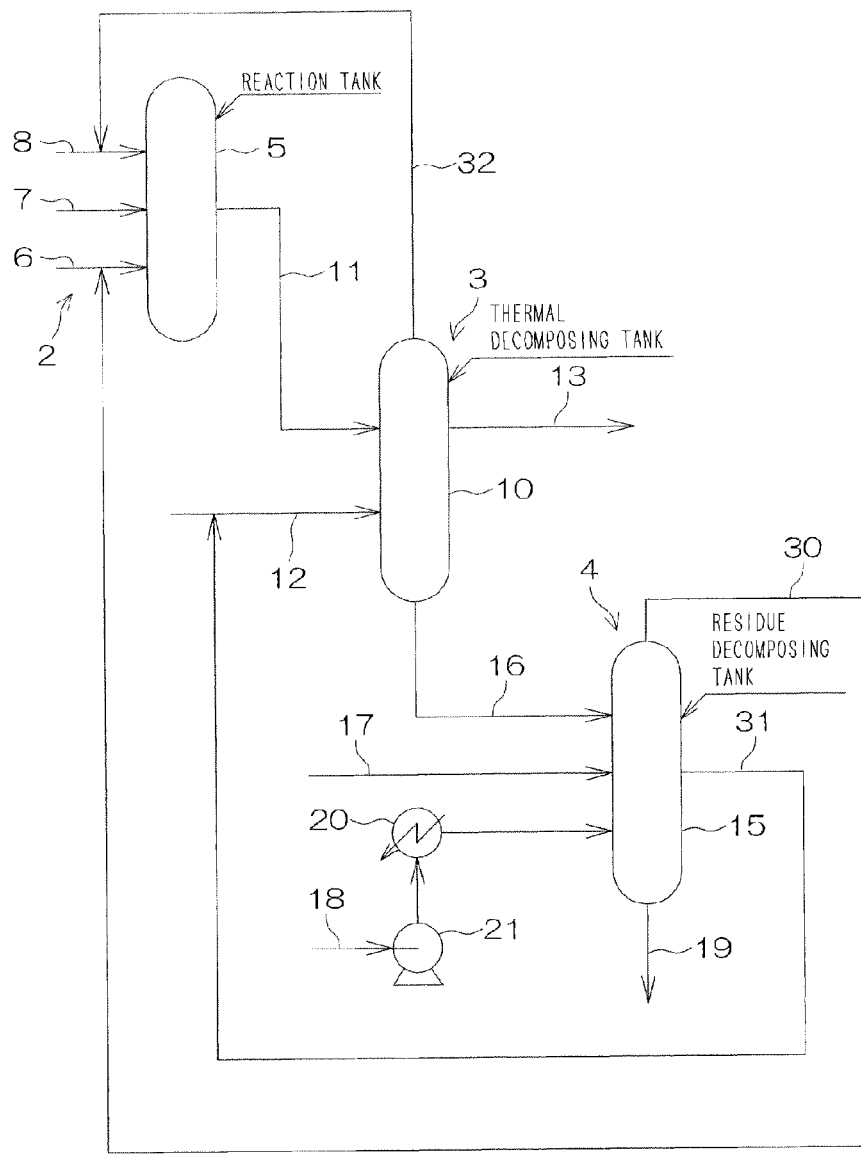
FIG. 1 is a schematic configuration diagram showing one embodiment of a plant employing a method for treating isocyanate residues according to the present invention.

In the method for treating isocyanate residues according to the present invention, isocyanate residues are hydrolyzed by contact with high pressure and high temperature water to give amine (described later) and alcohol (described later).

In such method for treating isocyanate residues, the isocyanate residues can be obtained by separating isocyanate (described later) and alcohol (described later) from a decomposition solution resulting from thermal decomposition reaction of carbamate.

The carbamate is an organic compound having at least one urethane bond (—NHCOO—) in its molecule, and is formed by a urea method, that is, a carbamate formation reaction of amine, urea and/or N-unsubstituted carbamic acid ester, and alcohol.

Examples of the amine include a primary amine.

The primary amine is an amino group-containing organic compound which has at least one primary amino group and is represented, for example, by the following general formula (1):

$$R^1-(NH_2)_n \quad (1)$$

(wherein $R^1$ represents an aliphatic hydrocarbon group having 1 to 15 total carbon atoms, an alicyclic-containing hydrocarbon group having 3 to 15 total carbon atoms, or an aromatic ring-containing hydrocarbon group having 6 to 15 total carbon atoms; and n represents an integer of 1 to 6.)

In formula (1) above, $R^1$ is selected from among the aliphatic hydrocarbon group having 1 to 15 total carbon atoms, the alicyclic-containing hydrocarbon group having 3 to 15 total carbon atoms, and the aromatic ring-containing hydrocarbon group having 6 to 15 total carbon atoms. $R^1$ may contain a stable linkage such as an ether linkage, a thioether linkage, or an ester linkage in the hydrocarbon group, and may be substituted with a stable functional group (described later).

In $R^1$, examples of the aliphatic hydrocarbon group having 1 to 15 total carbon atoms include linear or branched, monovalent to hexavalent aliphatic hydrocarbon groups having 1 to 15 total carbon atoms.

More specifically, examples thereof include an alkyl group having 1 to 15 total carbon atoms, an alkenyl groups having 1 to 15 total carbon atoms, and an alkylidene groups having 1 to 15 total carbon atoms.

Examples of the alkyl group include methyl, ethyl, propyl, iso-propyl, butyl, iso-butyl, sec-butyl, tert-butyl, pentyl, iso-pentyl, sec-pentyl, hexyl, heptyl, octyl, 2-ethylhexyl, nonyl, decyl, isodecyl, dodecyl, and tetradecyl.

Examples of the alkenyl group include propenyl, butenyl, and pentenyl.

Examples of the alkylidene group include ethylidene, propylidene, butylidene, pentylidene, and hexylidene.

Examples of the primary amine in which $R^1$ represents an aliphatic hydrocarbon group having 1 to 15 total carbon atoms in formula (1) above include aliphatic amines having 1 to 15 total carbon atoms.

Examples of the aliphatic amine include linear or branched aliphatic primary monoamines such as methylamine, ethylamine, n-propylamine, iso-propylamine, butylamine, pentylamine, hexylamine, n-octylamine, 2-ethylhexylamine, decylamine, dodecylamine, and tetradecylamine; aliphatic primary diamines such as 1,2-diaminoethane, 1,3-diaminopropane, 1,4-diaminobutane (1,4-tetramethylenediamine), 1,5-diaminopentane (1,5-pentamethylenediamine), 1,6-diaminohexane (1,6-hexamethylenediamine), 1,7-diaminoheptane, 1,8-diaminooctane, 1,9-diaminononane, 1,10-diaminodecane, 1,12-diaminododecane, 2,2,4-trimethyl hexamethylenediamine, 2,4,4-trimethyl hexamethylenediamine, and tetramethylenediamine; and aliphatic primary triamines such as 1,2,3-triaminopropane, triaminohexane, triaminononane, triaminododecane, 1,8-diamino-4-aminomethyloctane, 1,3,6-triaminohexane, 1,6,11-triaminododecane, and 3-aminomethyl-1,6-diaminohexane.

In $R^1$, examples of the alicyclic-containing hydrocarbon group having 3 to 15 total carbon atoms include monovalent to hexavalent alicyclic-containing hydrocarbon groups having 3 to 15 total carbon atoms.

The alicyclic-containing hydrocarbon group is merely required to contain at least one alicyclic hydrocarbon in the hydrocarbon group and, for example, an aliphatic hydrocarbon group or the like may be attached to the alicyclic hydrocarbon. In such case, the amino group of the primary amine may be either directly attached to the alicyclic hydrocarbon or attached to an aliphatic hydrocarbon group which is attached to the alicyclic hydrocarbon, or both.

More specifically, examples thereof include a cycloalkyl group having 3 to 15 total carbon atoms.

Examples of the cycloalkyl group include cyclopropyl, cyclobutyl, cyclopentyl, cyclohexyl, methylcyclohexyl, cyclooctyl, dimethylcyclohexyl, isophorone, norbornene, decalin, adamantane, 4,4'-methylenebis(cyclohexane), 2,4"-methylenebis(cyclohexane), and 1,4-cyclohexylidene.

Examples of the primary amine in which $R^1$ represents an alicyclic-containing hydrocarbon group having 3 to 15 total carbon atoms in formula (1) above include alicyclic amines having 3 to 15 total carbon atoms.

Examples of the alicyclic amine include alicyclic primary monoamines such as cyclopropylamine, cyclobutylamine, cyclopentylamine, cyclohexylamine, and hydrogenated toluidine; alicyclic primary diamines such as diaminocyclobutane, isophoronediamine (3-aminomethyl-3,5,5-trimethylcyclohexylamine), 1,2-diaminocyclohexane, 1,3-diaminocyclohexane, 1,4-diaminocyclohexane, 1,3-bis(aminomethyl)cyclohexane, 1,4-bis(aminomethyl)cyclohexane, 4,4'-methylenebis(cyclohexylamine), 2,5-bis(aminomethyl)bicyclo[2,2,1]heptane, 2,6-bis(aminomethyl)bicyclo[2,2,1]heptane, hydrogenated 2,4-tolylenediamine, and hydrogenated 2,6-tolylenediamine; and alicyclic primary triamine such as triaminocyclohexane.

In $R^1$, examples of the aromatic ring-containing hydrocarbon group having 6 to 15 total carbon atoms include monovalent to hexavalent aromatic ring-containing hydrocarbon groups having 6 to 15 total carbon atoms.

The aromatic ring-containing hydrocarbon group is merely required to contain at least one aromatic hydrocarbon in the hydrocarbon group and, for example, an aliphatic hydrocarbon group or the like is attached to the aromatic hydrocarbon. In such case, the amino group of the primary amine may be either directly attached to the aromatic hydrocarbon or attached to an aliphatic hydrocarbon group which is attached to the aromatic hydrocarbon, or both.

More specifically, examples thereof include an aryl group having 6 to 15 total carbon atoms.

Examples of the aryl group include phenyl, tolyl, xylyl, naphthyl, biphenyl, anthryl, trimethylphenyl, 4,4'-methylenebis phenylene, and phenanthryl.

Examples of the primary amine in which $R^1$ represents an aromatic ring-containing hydrocarbon group having 6 to 15 total carbon atoms in formula (1) above include aromatic amines having 6 to 15 total carbon atoms and aralkyl amines having 6 to 15 total carbon atoms.

Examples of the aromatic amine include aromatic primary monoamines such as aniline, o-toluidine (2-methylaniline), m-toluidine (3-methylaniline), p-toluidine (4-methylaniline), 2,3-xylidine (2,3-dimethylaniline), 2,4-xylidine (2,4-dimethylaniline), 2,5-xylidine (2,5-dimethylaniline), 2,6-xylidine (2,6-dimethylaniline), 3,4-xylidine (3,4-dimethylaniline), 3,5-xylidine (3,5-dimethylaniline), 1-naphthylamine, and 2-naphthylamine; and aromatic primary diamines such as 2,4-tolylenediamine(2,4-diaminotoluene), 2,6-tolylenediamine(2,6-diaminotoluene), 4,4'-diphenylmethanediamine, 2,4'-diphenylmethanediamine, 2,2'-diphenylmethanediamine, 4,4'-diphenyletherdiamine, 2-nitrodiphenyl-4,4'-diamine, 2,2'-diphenylpropane-4,4'-diamine, 3,3'-dimethyldiphenylmethane-4,4'-diamine, 4,4'-diphenylpropanediamine, m-phenylenediamine, p-phenylenediamine, naphthylene-1,4-diamine, naphthylene-1,5-diamine, and 3,3'-dimethoxydiphenyl-4,4'-diamine.

Examples of the aralkyl amine include aralkyl primary monoamines such as benzyl amine; aralkyl primary diamines such as 1,3-bis(aminomethyl)benzene, 1,4-bis(aminomethyl)benzene, 1,3-tetramethylxylylenediamine (1,3-di(2-amino-2-methylethyl)benzene), and 1,4-tetramethyl xylylenediamine (1,4-bis(2-amino-2-methylethyl)benzene).

Examples of the functional group that may be substituted at $R^1$ in formula (1) above include a nitro group, a hydroxyl group, a mercapto group, an oxo group, a thioxo group, a cyano group, a carboxy group, alkoxy-carbonyl group (e.g., an alkoxycarbonyl group having 2 to 4 total carbon atoms such as a methoxycarbonyl group and an ethoxycarbonyl group), a sulfo group, a halogen atom (e.g., fluorine, chlorine, bromine, and iodine), a lower alkoxy group (e.g., a methoxy group, an ethoxy group, a propoxy group, a butoxy group, an iso-butoxy group, a sec-butoxy group, and a tert-butoxy group), an aryloxy group (e.g., a phenoxy group), a halogenophenoxy group (e.g., o-, m- or p-chlorophenoxy group, and o-, m-, or p-bromophenoxy group), a lower alkylthio group (e.g., a methylthio group, an ethylthio group, an n-propylthio group, an iso-propylthio group, n-butylthio group, and a tert-butylthio group), an arylthio group (e.g., phenylthio group), a lower alkyl sulfinyl group (e.g., a methyl sulfinyl group and an ethyl sulfinyl group), a lower alkyl sulfonyl group (e.g., a methylsulfonyl group and an ethylsulfonyl group), an aryl sulfonyl group (e.g., phenyl slufonyl), a lower acyl group (e.g., a formyl group and an acetyl group), and an arylcarbonyl group (e.g., benzoyl group).

These functional groups may be multiply substituted at $R^1$ in formula (1) above. When the functional groups are multiply substituted at $R^1$, the functional groups may be the same or different from each other.

In formula (1) above, n represents an integer of, for example, 1 to 6, preferably, 1 or 2, or more preferably 2.

These amines may be used alone or in combination of two or more kinds.

Preferred examples of the amine include, in formula (1) above, a primary amine in which $R^1$ represents an alicyclic-containing hydrocarbon group having 3 to 15 total carbon atoms and a primary amine in which $R^1$ represents an aromatic ring-containing hydrocarbon group having 6 to 15 total carbon atoms. More specifically, examples thereof include an alicyclic amine having 3 to 15 total carbon atoms, an aromatic amine having 6 to 15 total carbon atoms, and an aralkyl amine having 6 to 15 total carbon atoms.

Further, as the amine, those industrially used as raw materials for producing isocyanates (described later) are preferable, and examples of such primary amine include 1,5-diaminopentane, 1,6-diaminohexane, isophoronediamine, 1,3-bis(aminomethyl)cyclohexane, 1,4-bis(aminomethyl)cyclohexane, 4,4'-methylenebis(cyclohexylamine), 2,5-bis(aminomethyl)bicyclo[2,2,1]heptane, 2,6-bis(aminomethyl)bicyclo[2,2,1]heptane, 2,4-tolylenediamine(2,4-diaminotoluene), 2,6-tolylenediamine(2,6-diaminotoluene), 4,4'-diphenylmethanediamine, 2,4'-diphenylmethanediamine, 2,2'-diphenylmethanediamine, naphthylene-1,5-diamine, 1,3-bis(aminomethyl)benzene, 1,4-bis(aminomethyl)benzene, 1,3-tetramethylxylylenediamine, and 1,4-tetramethylxylylenediamine. In particular, isophoronediamine, 2,4-tolylenediamine(2,4-diaminotoluene), 2,6-tolylenediamine(2,6-diaminotoluene), 4,4'-diphenylmethanediamine, 2,4'-diphenylmethanediamine, 2,2'-diphenylmethanediamine, naphthylene-1,5-diamine, 1,3-bis(aminomethyl)benzene, 1,4-bis(aminomethyl)benzene, 1,3-tetramethylxylylenediamine, and 1,4-tetramethylxylylenediamine are preferable.

Although will be described in detail later, an amine (described later) obtained by decomposing isocyanate residues (described later) is preferable as the amine used for production of the carbamate.

The N-unsubstituted carbamic acid ester is a carbamic acid ester in which a nitrogen atom of a carbamoyl group is not substituted with a functional group (i.e., the nitrogen atom is bonded to two hydrogen atoms and one carbon atom), and is represented, for example, by the following general formula (2):

$$R^2O\text{—}CO\text{—}NH_2 \quad (2)$$

(wherein $R^2$ represents an alkyl group, or an aryl group which may have a substituent.)

Examples of the alkyl group represented by $R^2$ in formula (2) above include a linear or branched saturated hydrocarbon group having 1 to 8 carbon atoms such as methyl, ethyl, n-propyl, iso-propyl, n-butyl, iso-butyl, sec-butyl, tert-butyl, pentyl, hexyl, heptyl, octyl, iso-octyl, and 2-ethylhexyl; and an alicyclic saturated hydrocarbon group having 5 to 10 carbon atoms such as cyclohexyl and cyclododecyl.

As the alkyl group represented by $R^2$, a linear or branched saturated hydrocarbon group having 1 to 8 carbon atoms is preferable, a linear or branched saturated hydrocarbon group having 2 to 6 carbon atoms is more preferable, or a linear saturated hydrocarbon group having 2 to 6 carbon atoms is even more preferable.

Examples of the N-unsubstituted carbamic acid ester in which $R^2$ represents an alkyl group in formula (2) above include N-unsubstituted carbamic acid esters containing a saturated hydrocarbon such as methyl carbamate, ethyl carbamate, n-propyl carbamate, iso-propyl carbamate, n-butyl carbamate, iso-butyl carbamate, sec-butyl carbamate, tert-butyl carbamate, pentyl carbamate, hexyl carbamate, heptyl carbamate, octyl carbamate, iso-octyl carbamate, and 2-ethylhexyl carbamate; and N-unsubstituted carbamic acid esters containing an alicyclic saturated hydrocarbon such as cyclohexyl carbamate and cyclododecyl carbamate.

Examples of the aryl group which may have a substituent, represented by $R^2$ in formula (2) above, include aryl groups having 6 to 18 carbon atoms such as phenyl, tolyl, xylyl, biphenyl, naphthyl, anthryl, and phenanthryl. Further, examples of the substituent include a hydroxyl group, a halogen atom (e.g., chlorine, fluorine, bromine, and iodine), a cyano group, an amino group, a carboxyl group, an alkoxy group (e.g., an alkoxy group having 1 to 4 carbon atoms such as a methoxy, an ethoxy, a propoxy, or a butoxy group), an aryloxy group (e.g., a phenoxy group etc.), an alkylthio group (e.g., an alkylthio group having 1 to 4 carbon atoms such as a methylthio, an ethylthio, a propylthio, or a butylthio group), and an arylthio group (e.g., phenylthio group). When the substituents are multiply substituted at the aryl group, the substituents may be the same or different from each other.

Examples of the N-unsubstituted carbamic acid ester whose $R^2$ represents an aryl group which may have a substituent in formula (2) above include N-unsubstituted carbamic acid esters containing an aromatic hydrocarbon such as phenyl carbamate, tolyl carbamate, xylyl carbamate, biphenyl carbamate, naphthyl carbamate, anthryl carbamate, and phenanthryl carbamate.

These N-unsubstituted carbamic acid esters can be used alone or in combination of two or more kinds.

As the N-unsubstituted carbamic acid ester, N-unsubstituted carbamic acid ester in which $R^2$ represents an alkyl group in formula (2) above is preferable.

Further, as the N-unsubstituted carbamic acid ester used as a raw material component for the carbamate formation reaction, N-unsubstituted carbamic acid ester obtained by further separating from low boiling components (described later) (containing N-unsubstituted carbamic acid ester and carbonate) which have been separated after the carbamate formation reaction is preferable, although will be described in detail later.

The alcohol is, for example, a primary to tertiary monohydric alcohol and is, for example, represented by the following general formula (3):

$$R^2\text{—OH} \qquad (3)$$

(wherein $R^2$ is defined as $R^2$ in formula (2) above.)

In formula (3) above, $R^2$ is defined as $R^2$ in formula (2) above, that is, represents an alkyl group, or an aryl group which may have a substituent.

Examples of the alcohol in which $R^2$ represents the alkyl group in formula (3) above include alcohols containing a linear or branched saturated hydrocarbon, such as methanol, ethanol, n-propanol, iso-propanol, n-butanol (1-butanol), iso-butanol, sec-butanol, tert-butanol, pentanol, hexanol, heptanol, octanol, iso-octanol, and 2-ethylhexanol; and alcohols containing an alicyclic saturated hydrocarbon, such as cyclohexanol and cyclododecanol.

Further, examples of the alcohol whose $R^2$ represents the above-mentioned aryl group which may have a substituent in formula (3) above include phenol, hydroxytoluene, hydroxyxylene, biphenyl alcohol, naphthalenol, anthracenol, and phenanthrenol.

These alcohols can be used alone or in combination of two or more kinds.

As the alcohol, in formula (3) above, an alcohol in which $R^2$ represents an alkyl group is preferable, an alcohol in which $R^2$ represents an alkyl group having 1 to 8 carbon atoms is more preferable, or an alcohol in which $R^2$ represents an alkyl group having 2 to 6 carbon atoms is even more preferable.

As the alcohol used as a raw material component for the carbamate formation reaction, an alcohol (described later) obtained by hydrolyzing the isocyanate residues blended with carbonate is preferable.

Further, preferred examples thereof include an alcohol (described later) by-produced when N-unsubstituted carbamic acid ester is used as a raw material component in the carbamate formation reaction, and an alcohol (described later) separated from the decomposition solution resulting from the thermal decomposition reaction of the carbamate.

In this method, the amine, urea and/or N-unsubstituted carbamic acid ester, and alcohol described above are blended and the blended mixture is allowed to react preferably in a liquid phase.

The amounts of the amine, urea and/or N-unsubstituted carbamic acid ester, and alcohol are not particularly limited and can be appropriately selected over a relatively wide range.

Usually, the amounts of the urea and the N-unsubstituted carbamic acid ester, and the amount of the alcohol may be equimolar or more to the amount of the amino group in the amine, so that the urea and/or the N-unsubstituted carbamic acid ester, and the alcohol themselves can also be used as reaction solvents in this reaction.

When the urea and/or the N-unsubstituted carbamic acid ester and the alcohol also serve as the reaction solvents, excess amounts of the urea and/or the N-unsubstituted carbamic acid ester and the alcohol are used as required. Large excess amounts thereof however, increase consumption energy in the separation step after the reaction, which may be unsuitable for industrial production.

Therefore, from the viewpoint of improving the yield of the carbamate, the amount(s) of the urea and/or the N-unsubstituted carbamic acid ester is/are of the order of 0.5 to 20 times moles, preferably 1 to 10 times moles, or more preferably 1 to 5 times moles with respect to one amino group of the amine, and the amount of the alcohol is of the order of 0.5 to 100 times moles, preferably 1 to 20 times moles, or more preferably 1 to 10 times moles, with respect to one amino group of the amine.

In this reaction, although a reaction solvent is not necessarily required, for example, when reaction raw materials are solid or when a reaction product is deposited, blending of the reaction solvent can improve operability.

Such reaction solvent is not particularly limited as long as it is inert to or has poor reactivity to the primary amine, urea and/or N-unsubstituted carbamic acid ester, and alcohol, which are reaction raw materials, and to the carbamate which is a reaction product, and examples thereof include aliphatic hydrocarbons (e.g., hexane, pentane, petroleum ether, ligroin, cyclododecane, and decalins); aromatic hydrocarbons (e.g., benzene, toluene, xylene, ethylbenzene, isopropyl benzene, butylbenzene, cyclohexylbenzene, tetralin, chlorobenzene, o-dichlorobenzene, methylnaphthalene, chloronaphthalene, dibenzyltoluene, triphenylmethane, phenylnaphthalene, biphenyl, diethylbiphenyl, and triethylbiphenyl); ethers (e.g., diethyl ether, diisopropyl ether, dibutyl ether, anisole, diphenyl ether, tetrahydrofuran, ethylene glycol dimethyl ether, ethylene glycol diethyl ether, ethylene glycol dibutyl ether, diethylene glycol dimethyl ether, and diethylene glycol diethyl ether); carbonates (e.g., dimethyl carbonate, diethyl carbonate, dipropyl carbonate, and dibutyl carbonate); nitriles (e.g., acetonitrile, propionitrile, adiponitrile, and benzonitrile); aliphatic halogenated hydrocarbons (e.g., methylene chloride, chloroform, 1,2-dichloroethane, 1,2-dichloropropane, and 1,4-dichlorobutane); amides (e.g., dimethylformamide and dimethylacetamide); nitro compounds (e.g., nitromethane and nitrobenzene); N-methylpyrrolidinone, N,N-dimethylimidazolidinone, and dimethyl sulfoxide.

Among these reaction solvents, aliphatic hydrocarbons and aromatic hydrocarbons are preferably used in consideration of economical efficiency, operability, or the like. These reaction solvents can also be used alone or in combination of two or more kinds.

The amount of the reaction solvent is not particularly limited as long as it is sufficient for the carbamate as a desired product to be dissolved. Industrially, the amount of the reaction solvent is preferably minimized as much as possible in view that since it is necessary to recover the reaction solvent from the reaction solution, the energy consumed for the recovery can be reduced as much as possible, and in view that a large amount of the reaction solvent can decrease substrate concentration on the reaction to slow the reaction rate. More specifically, the amount of the reaction solvent is usually in the range of 0 to 500 parts by mass, or preferably 0 to 100 parts by mass, per 1 part by mass of the amine.

In this reaction, the reaction temperature is appropriately selected from the range of 100 to 350° C., or preferably 150 to 300° C. When the reaction temperature is lower than this range, the reaction rate may decrease. On the other hand, when it is higher than this range, a side reaction increases, so that the yield of the carbamate as a desired product may be reduced.

The reaction is usually carried out under atmospheric pressure. However, when the boiling point of the component in the reaction solution is lower than the reaction temperature, the reaction may be carried out under an increased pressure or, if necessary, under a reduced pressure.

The reaction time is in the range of, for example, 0.1 to 20 hours, or preferably 0.5 to 10 hours. When the reaction time is shorter than this range, the yield of the carbamate as a desired product may be reduced. On the other hand, when it is longer than this range, the reaction is unsuitable for industrial production.

In this method, a catalyst can also be used.

No particular limitation is imposed on the catalyst, and examples thereof include lithium methanolate, lithium ethanolate, lithium propanolate, lithium butanolate, sodium methanolate, potassium-tert-butanolate, magnesium methanolate, calcium methanolate, tin(II) chloride, tin(IV) chloride, lead acetate, lead phosphate, antimony(III) chloride, antimony(V) chloride, aluminium acetylacetonate, aluminium-isobutylate, aluminum trichloride, bismuth(III) chloride, copper(II) acetate, copper(II) sulfate, copper(II) nitrate, bis(triphenyl-phosphinoxide)-copper(II) chloride, copper molybdate, silver acetate, gold acetate, zinc oxide, zinc chloride, zinc acetate, zinc acetonylacetate, zinc octanoate, zinc oxalate, zinc hexylate, zinc benzoate, zinc undecylenate, cerium(IV) oxide, uranyl acetate, titanium tetraisopropanolate, titanium tetrabutanolate, titanium tetrachloride, titanium tetraphenolate, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron(II) acetate, iron(III) acetate, iron phosphate, iron oxalate, iron (III) chloride, iron(III) bromide, cobalt acetate, cobalt chloride, cobalt sulfate, cobalt naphthenate, nickel chloride, nickel acetate, and nickel naphthenate.

Further, examples of the catalyst include $Zn(OSO_2CF_3)_2$ (also known as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

These catalysts can be used alone or in combination of two or more kinds.

The amount of the catalyst is in the range of, for example, 0.000001 to 0.1 mol, or preferably 0.00005 to 0.05 mol, per 1 mol of the amine. Even if the amount of the catalyst is more than the above range, no further remarkable reaction enhancing effect is observed, but cost may increase due to an increase in the amount. On the other hand, when the amount is less than the above range, the reaction enhancing effect may not be obtained.

The method for adding the catalyst is not particularly limited, and the method of each of package addition, continuous addition, and intermittent addition in portions does not affect the reaction activity.

Then, this reaction may be carried out, for example, by charging amine, urea and/or N-unsubstituted carbamic acid ester, alcohol, if necessary, a catalyst and a reaction solvent, in a reaction vessel under the above-mentioned conditions, and stirring or mixing the charged mixture. A carbamate represented, for example, by the following general formula (4) is predominantly produced:

   (4)

(wherein $R^1$ is defined as $R^1$ in formula (1) above; $R^2$ is defined as $R^2$ in formula (2) above; and n is defined as n in formula (1) above.)

Specific examples of the carbamate include aliphatic carbamates such as methyl hexyl carbamate, methyl octyl carbamate, methyl dodecyl carbamate, methyl octadecyl carbamate, 1,4-bis(methoxycarbonylamino)butane, 1,4-bis (ethoxycarbonylamino)butane, 1,4-bis (butoxycarbonylamino)butane, 1,5-bis(methoxycarbonylamino)pentane, 1,5-bis (butoxycarbonylamino)pentane, 1,6-bis(methoxycarbonylamino)hexane, 1,6-bis (ethoxycarbonylamino)hexane, 1,6-bis(butoxycarbonylamino)hexane, 1,8-bis (methoxycarbonylamino)octane, 1,8-bis(butoxycarbonylamino)octane, 1,8-bis (phenoxycarbonylamino)-4-(phenoxycarbonylaminomethyl)octane, 1,9-bis (methoxycarbonylamino)nonane, 1,9-bis(butoxycarbonylamino) nonane, 1,10-bis (methoxycarbonylamino)-decane, 1,12-bis (butoxycarbonylamino)-dodecane, 1,12-bis (methoxycarbonylamino)-dodecane, 1,12-bis(phenoxycarbonylamino)-dodecane, 2,2'-bis (4-propoxycarbonylaminophenyl)propane, 1,3,6-tris(methoxycarbonylamino)hexane, and 1,3,6-tris(phenoxycarbonylamino)hexane; alicyclic carbamates such as 1,3- or 1,4-bis (methoxycarbonylamino) cyclohexane, 1,3- or 1,4-bis(ethoxycarbonylamino)cyclohexane, 1,3- or 1,4-bis(butoxycarbonylamino)cyclohexane, 1,3- or 1,4-bis(methoxycarbonylaminomethyl)cyclohexane, 1,3- or 1,4-bis(ethoxycarbonylaminomethyl)cyclohexane, 1,3- or 1,4-bis (butoxycarbonylaminomethyl)cyclohexane, 2,4'- or 4,4'-bis(ethoxycarbonylamino)dicyclohexanemethane, 2,4'- or 4,4'-bis(phenoxycarbonylamino)dicyclohexylmethane, 2,4'- or 4,4'-bis(methoxycarbonylamino) dicyclohexyl methane, 2,4'- or 4,4'-bis (butoxycarbonylamino)dicyclohexyl methane, 2,5-bis (methoxycarbonylaminomethyl)bicyclo[2,2,1]heptane, 2,5-bis (butoxycarbonylaminomethyl)bicyclo[2,2,1]heptane, 2,6-bis(methoxycarbonylaminomethyl)bicyclo[2,2,1] heptane, 2,6-bis(bobutoxycarbonylaminomethyl)bicyclo[2,2,1]heptane, 1-(methoxycarbonylamino)-3,3,5-trimethyl-5-(methoxycarbonylaminomethyl)-cyclohexane, 1-(butoxycarbonylamino)-3,3,5-trimethyl-5-(butoxycarbonylaminomethyl)-cyclohexane, 3-methoxycarbonylaminomethyl-3,5,5-trimethyl-1-methoxycarbonylaminocyclohexane, 4,4'-bis (methoxycarbonylamino)-2,2'-dicyclohexylpropane, and 4,4'-bis (butoxycarbonylamino)-2,2'-dicyclohexylpropane; and aromatic carbamates such as 1,3- or 1,4-bis(methoxycarbonylaminomethyl)benzene, 1,3- or 1,4-bis(ethoxycarbonylaminomethyl)benzene, 1,3- or 1,4-bis(butoxycarhonylaminomethyl)benzene, 1,3- or 1,4-bis (methoxyearhonylamino)benzene, 1,3- or 1,4-bis(butoxycarbonylamino)benzene, 2,4'- or 4,4'-bis(methoxycarbonylamino)diphenylmethane, 2,4'- or 4,4'-bis(ethoxycarhonylamino)diphenylmethane, 2,4'- or 4,4'-bis (butoxycarhonylamino)diphenylmethane, 4,4'-bis (phenoxycarbonylamino)diphenylmethane, 1,5- or 2,6-bis (methoxycarbonylamino)naphthalene, 1,5- or 2,6-bis(butoxycarbonylamino)naphthalene, 4,4'-bis(nethoxycarbonylamino)biphenyl, 4,4'-bis(butoxycarhonylamino)biphenyl, 2,4- or 2,6-bis(methoxycarbonylamino)toluene, 2,4- or 2,6-bis(ethoxycarhonylamino)toluene, and 2,4- or 2,6-bis(butoxycarbonylamino)toluene.

In this reaction, ammonia is by-produced.

Further when N-unsubstituted carbamatic acid ester is blended in this reaction, an alcohol represented, for example, by the following general formula (5) is by-produced:

   (5)

(wherein $R^2$ is defined as $R^2$ in formula (2) above.)

In this reaction, for example, an N-unsubstituted carbamic acid ester represented by the following general formula (6) is by-produced:

   (6)

(wherein $R^2$ is defined as $R^2$ in formula (2) above.)

Further, in this reaction, a carbonate represented by the following general formula (7) is by-produced:

   (7)

(wherein $R^2$ may be the same or different from each other, and $R^2$ is defined as $R^2$ in formula (2) above.)

In formula (7) above, $R^2$ may be the same or different from each other, and $R^2$ is defined as $R^2$ in formula (2) above, that is, $R^2$ may be the same or different from each other and each represents an alkyl group, or an aryl group which may have a substituent.

When each $R^2$ is an alkyl group in formula (7) above, the carbonate represented by formula (7) above is dialkyl carbonate to be described later; when each $R^2$ is an aryl group which may have a substituent, the carbonate represented by formula (7) above is diaryl carbonate to be described later; and further, when one $R^2$ is an alkyl group and another $R^2$ is an aryl group which may have a substituent, the carbonate represented by formula (7) above is alkyl aryl carbonate to be described later.

In this reaction, either of a batch reaction process or a continuous reaction process can be adopted.

Next, in this method, while the carbamate (formula (4) above) is separated from the obtained reaction solution by a known method, for example, excess (unreacted) urea and/or N-unsubstituted carbamic acid ester and excess (unreacted) alcohol; and alcohol (formula (5) above), N-unsubstituted carbamic acid ester (formula (6) above), and carbonate (formula (7) above) which are by-produced are separated as low boiling components (light-boiling fractions).

Then, in this method, the obtained carbamate is thermally decomposed to produce an isocyanate and an alcohol.

Specifically, in this method, for example, the carbamate obtained by the above-mentioned method is thermally decomposed, and an isocyanate represented by the following general formula (8) corresponding to the above-mentioned amine:

$$R^1\text{—(NCO)}n \qquad (8)$$

(wherein $R^1$ is defined as $R^1$ in formula (1) above, and n is defined as n in formula (1) above.)
and an alcohol represented by the following general formula (9) which is a by-product are produced.

$$R^2\text{—OH} \qquad (9)$$

(wherein $R^2$ is defined as $R^2$ in formula (2) above.)

No particular limitation is imposed on the thermal decomposition. Known decomposition methods such as a liquid phase method and a vapor phase method can be used.

In the vapor phase method, the isocyanate and alcohol produced by the thermal decomposition can be separated from a gaseous product mixture by fractional condensation. In the liquid phase method, the isocyanate and alcohol produced by the thermal decomposition can be separated, for example, by distillation or using a solvent and/or inert gas as a support substance.

As the thermal decomposition, a liquid phase method is preferable from the viewpoint of workability.

In such method, the carbamate is thermally decomposed preferably in the presence of an inert solvent.

The inert solvent is not particularly limited as long as it dissolves at least the carbamate, is inert to the carbamate and the isocyanate, and remains unreacted (i.e., stable) during the thermal decomposition. For efficient thermal decomposition reaction, the inert solvent preferably has a higher boiling point than the isocyanate to be produced.

As such inert solvent, aromatic hydrocarbons may be used.

Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237-340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 241° C.), 1-chloronaphthalene (boiling point: 263° C.), 2-chloronaphthalene (boiling point: 264-266° C.), triphenylmethane (boiling point: 358-359° C. (754 mmHg)), 1-phenylnaphthalene (boiling point: 324-325° C.), 2-phenylnaphthalene (boiling point: 357-358° C.), and biphenyl (boiling point: 255° C.).

These solvents are also available as commercially available products and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.), Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 2H (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove manufactured by Matsumura Oil Co., Ltd.); and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KSK-OIL 280 (aromatic hydrocarbon, boiling point: 303° C.) (hereinabove, manufactured by Soken Tecnix Co., Ltd.).

Further, examples of the inert solvent include esters (e.g., dioctyl phthalate, didecyl phthalate, and didodecyl phthalate) and aliphatic hydrocarbons which are commonly used as a heat transfer medium.

These inert solvents can be used alone or in combination of two or more kinds.

As the inert solvent, the same type of solvent as a solvent (described later) used in decomposition of isocyanate residues (described later) is preferable, or a solvent (described later) to be separated and recovered after isocyanate residues (described later) are decomposed is more preferable.

That is, preferably, the carbamate is thermally decomposed in the presence of the solvent (described later) to be recovered after isocyanate residues (described later) are decomposed.

The amount of the inert solvent is in the range of 0.001 to 100 parts by mass, preferably 0.01 to 80 parts by mass, or more preferably 0.1 to 50 parts by mass, per 1 part by mass of the carbamate.

In the thermal decomposition, for example, the inert solvent is blended with the carbamate, the blended carbamate is thermally decomposed. Thereafter, the inert solvent is separated and recovered, and then again can be blended with the carbamate in the thermal decomposition.

Since the thermal decomposition reaction of the carbamate in the liquid phase method is a reversible reaction, preferably, the carbamate is thermally decomposed and, to suppress a reverse reaction (i.e. the urethane-forming reaction between the isocyanate represented by formula (8) above and the alcohol represented by formula (9) above) to the thermal decomposition reaction, at the same time, the isocyanate represented by formula (8) above and/or the alcohol represented by formula (9) above are drawn out of the reaction mixture (decomposition solution) and then separated.

As the reaction condition of the thermal decomposition reaction, preferable are reaction conditions such that the carbamate can be thermally decomposed in an excellent manner, and at the same time, the isocyanate (formula (8) above) and alcohol (formula (9) above) produced by the thermal decomposition process evaporate, whereby the carbamate and the isocyanate fail to reach equilibrium, and further, a side reaction such as polymerization of isocyanates is suppressed.

As the reaction conditions, more specifically, the thermal decomposition temperature is usually 350° C. or lower, preferably from 80 to 350° C., or more preferably from 100 to 300° C. At the thermal decomposition temperature lower than 80° C., a practical reaction rate may not be obtained. On the other hand, at the thermal decomposition temperature higher than 350° C., an undesired side reaction such as polymerization of isocyanates may occur. It is preferable that the pressure during the thermal decomposition reaction is a pressure for allowing the alcohol produced to be vaporized at the thermal decomposition reaction temperature specified above. For practical use, the pressure is preferably in the range of 0.133 to 90 kPa in terms of equipment and utilities.

Further, in this method, if necessary, a catalyst may be added.

Although the catalyst varies depending on its kind, it may be added at any timing of during the above-mentioned reaction, before and after distillation and separation after the reaction, and before and after separation of the carbamate.

As the catalyst used for the thermal decomposition, at least one metal selected from the group consisting of Sn, Sb, Fe, Co, Ni, Cu, Cr, Ti, Pb, Mo, and Mn, or a metallic compound thereof such as oxide, halide, carboxylate, phosphate, and organometallic compound, used for the urethane-forming reaction of an isocyanate and a hydroxyl group is used. Among them, Fe, Sn, Co, Sb, and Mn are preferably used in the thermal decomposition because they exhibit the effect of suppressing the production of by-product.

Examples of the metallic catalyst of Sn include tin oxide, tin chloride, tin bromide, tin iodide, tin formate, tin acetate, tin oxalate, tin octylate, tin stearate, tin oleate, tin phosphorate, dibutyltin dichloride, dibutyltin dilaurate, and 1,1,3,3-tetrabutyl-1,3-dilauryloxydistannoxane.

Examples of the metallic catalysts of Fe, Co, Sb, and Mn include acetate, benzoate, naphthenate, and acetylacetonate thereof.

The amount of the catalyst is in the range of 0.0001 to 5% by mass, or preferably 0.001 to 1% by mass, per the reaction solution, as a metal or a compound thereof.

The thermal decomposition reaction can be carried out by a batch reaction process in which the carbamate, the catalyst, and the inert solvent are charged by a batch, or by a continuous reaction process in which the carbamate is charged into the inert solvent containing the catalyst under reduced pressure.

In the thermal decomposition, an isocyanate and an alcohol are produced and, for example, allophanate, amines, urea, carbonate, carbamate, and carbon dioxide may also be produced by a side reaction in some cases. Therefore, if necessary, the isocyanate thus produced is purified by a known method.

Examples of the isocyanate (general formula (8) above) thus produced include polymethylene polyphenylene isocyanate (MDI), tolylene diisocyanate (TDI), xylylene diisocyanate (XDI), tetramethylxylylene diisocyanate (TMXDI), bis (isocyanatomethyl)norbornane (NBDI), 3-isocyanatomethyl-3,5,5-trimethylcyclohexylisocyanate (IPDI), 4,4'-methylenebis(cyclohexylisocyanate) ($H_{12}$MDI), bis(isocyanatomethyl)cyclohexane ($H_6$XDI), hexamethylene diisocyanate (HDI), and pentamethylene diisocyanate (PDI), depending on the isocyanate (kinds of the carbamate (formula (4) above) as a decomposition target and the amine (formula (1) above) as a production raw material) produced at a production plant.

The alcohol (formula (9) above) obtained by the thermal decomposition is separated and recovered, and the recovered alcohol is then preferably used as a raw material component for the carbamate formation reaction.

Then, in this method, the isocyanate and the alcohol are removed from the decomposition solution resulting from the thermal decomposition reaction of the carbamate, and the solvent is separated therefrom as required, so that isocyanate residues are obtained. The separated solvent can be again used for the thermal decomposition.

That is, for example, in the case where carbamates are produced by reaction of amine, urea and/or N-unsubstituted carbamic acid ester, and alcohol, and the carbamate is thermally decomposed to produce an isocyanate, for example, the carbamate or isocyanate thus obtained, or intermediates thereof may cause unpreferable polymerization reaction such as for multimerization, biuretization, or allophanatization in some cases. In such a case, by-products such as urea derivatives (biuret derivatives) or carbamate derivatives (allophanate derivatives) are obtained as isocyanate residues. The isocyanate residues may contain, for example, unreacted urea or carbamate in some cases.

Although these isocyanate residues are usually disposed of, it is required that wastes should be reduced from the viewpoints of global environment or related factors and a method for effectively using recovered isocyanate residues is also desired.

Therefore, in this method, the obtained isocyanate residues are hydrolyzed by contact with high pressure and high temperature water to give amine and alcohol.

In the hydrolysis, preferably, the obtained isocyanate residues are decomposed into amine by contact with high pressure and high temperature water in the presence of a solvent.

The solvent is not particularly limited as long as it is inert or has poor reactivity to isocyanate groups or amino groups and also exhibits hydrolysis resistance (i.e., does not react during the hydrolysis of the isocyanate residues), and an aromatic hydrocarbon may be used.

Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237-340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 24 PC), 1-chloronaphthalene (boiling point: 263° C.), 2-chloronaphthalene (boiling point: 264-266° C.), triphenylmethane (boiling point: 358-359° C. (754 mmHg)), 1-phenylnaphthalene (boiling point: 324-325° C.), 2-phenylnaphthalene (boiling point: 357-358° C.), and biphenyl (boiling point: 255° C.).

These solvents are also available as commercially available products and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.), Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 2H (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove manufactured by Matsumura Oil Co., Ltd.); and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KSK-OIL 280 (aromatic hydrocarbon, boiling point: 303° C.) (hereinabove, manufactured by Soken Tecnix Co., Ltd.).

These solvents can be used alone or in combination of two or more kinds.

The amount of the solvent is in the range of 0.05 to 9.00 parts by mass, or preferably 0.10 to 5.00 parts by mass, per 1 part by mass of the isocyanate residues.

As the solvent in the decomposition of the isocyanate residues, the same type of solvent as that used in the thermal decomposition of the carbamate described above is preferable. In such case, more preferably, after the isocyanate residues are decomposed, the solvent is recovered and the solvent thus recovered is used for the thermal decomposition of the carbamate.

Therefore, when a solvent is used for decomposition of isocyanate residues, recovered after the decomposition, and again used for thermal decomposition of carbamate after recovered, cost efficiency and workability can be improved.

As such solvent, aromatic hydrocarbons having a boiling point of 250° C. or higher are preferable.

The use of an aromatic hydrocarbon having a boiling point of 250° C. or higher as the solvent can provide an excellent recovery of the isocyanate during the thermal decomposition of the carbamate.

The high pressure and high temperature water is water which is increased in pressure to a high pressure, that is, from 3 to 30 MPa, preferably from 6 to 25 MPa, or more preferably from 6 to 20 MPa, as well as in temperature to a high temperature, that is, from 190 to 350° C., or preferably from 200 to 300° C., and is heated and pressurized by a known method.

The decomposing pressure of the isocyanate residues is in the range of 3 to 30 MPa, preferably 6 to 25 MPa, or more preferably 6 to 20 MPa. The decomposing temperature of the isocyanate residues is in the range of 190 to 350° C., or preferably 200 to 300° C.

As the high pressure and high temperature water, a hydrolytic ratio (a mass ratio of (high pressure and high temperature water/isocyanate residues)) is controlled to, for example 0.5 to 10, or preferably 1 to 5.

As a result of this, the isocyanate residues are hydrolyzed with the high pressure and high temperature water to produce a corresponding amine as a decomposition product, during which carbon dioxide, water, etc. are by-produced.

At this time, when the isocyanate residues to be hydrolyzed are those obtained by thermally decomposing the carbamate which has been produced by the reaction of amine, urea and/or N-unsubstituted carbamic acid ester, and alcohol as described above, an amine represented by the following general formula (10) is produced as the corresponding amine:

$$R^1\text{—}(NH_2)n \quad (10)$$

(wherein $R^1$ is defined as $R^1$ in formula (1) above, and n is defined as n in formula (1) above.)

Examples of the amine include polymethylenepolyphenylene polyamine (MDA) corresponding to polymethylenepolyphenylene isocyanate (MDI), tolylene diamine (TDA) corresponding to tolylene diisocyanate (TDI), xylylene diamine (XDA) corresponding to xylylene diisocyanate (XDI), tetramethylxylylene diamine (TMXDA) corresponding to tetramethylxylylene diisocyanate (TMXDI), bis(aminomethyl)norbornane (NBDA) corresponding to bis(isocyanatomethyl)norbornane (NBDI), 3-aminomethyl-3,5,5-trimethylcyclohexyl amine (IPDA) corresponding to 3-isocyanatomethyl-3,5,5-trimethylcyclohexyl isocyanate (IPDI), 4,4'-methylenebis(cyclohexylamine) ($H_{12}$MDA) corresponding to 4,4'-methylenebis(cyclohexylisocyanate) ($H_{12}$MDI), bis(aminomethyl)cyclohexane ($H_6$XDA) corresponding to bis(isocyanatomethyl)cyclohexane ($H_6$XDI), hexamethylene diamine (HDA) corresponding to hexamethylene diisocyanate (HDI), and pentamethylene diamine (PDA) corresponding to pentamethylene diisocyanate.

In other words, when the isocyanate residues obtained by separating isocyanate and alcohol from the decomposition solution which has been obtained by the thermal decomposition reaction of the carbamate is decomposed, the same type of amine (general formula (10) above) as the amine (general formula (1) above) used for the production of the carbamate and the isocyanate may be obtained in some cases. In such cases, the amine obtained by decomposing the isocyanate residues is, after separated and recovered, preferably used as raw material amine (general formula (1) above) during the production of the carbamate described above.

A known method may be used to separate the amine, and distillation is preferable.

Further in this method, preferably, after the isocyanate residues are decomposed, the solvent is separated and recovered to be used for the thermal decomposition of the carbamate in consideration of economical efficiency, operability, etc. That is, in this method, the carbamate is thermally decomposed in the presence of the solvent recovered after the decomposition of the isocyanate residues.

In such thermal decomposition reaction, the carbamate obtained above is thermally decomposed, so that isocyanate corresponding to the amine can be obtained as described above. Therefore, for example, polyisocyanates industrially used as raw materials for polyurethane can be produced easily and efficiently.

FIG. 1 is a schematic configuration diagram showing one embodiment of a plant employing a method for treating isocyanate residues according to the present invention.

One embodiment of the plant in the case of industrially carrying out the above-mentioned method for treating isocyanate residues is described below with reference to FIG. 1.

In FIG. 1, this plant 1 is an isocyanate production system which produces an isocyanate by a urea method during which isocyanate residues are obtained, and applies the above-mentioned method for treating isocyanate residues to the isocyanate residues, and includes a reaction system 2, a thermal decomposing system 3, and a residue decomposing system 4.

The reaction system 2 is equipped in the plant 1, for the purpose of producing carbamates by reaction of amine, urea and/or N-unsubstituted carbamic acid ester, and alcohol.

The reaction system 2 includes a reaction tank 5, and an amine feed pipe 6, a urea feed pipe 7, and an alcohol feed pipe 8 which are connected to the reaction tank 5.

The reaction tank 5 is a carbamate formation reaction tank for carbamates to be produced by carbamate formation reaction of amine, urea and/or N-unsubstituted carbamic acid ester, and alcohol. It has a heat-resistant and pressure-resistant vessel whose temperature and pressure can be controlled.

Though not shown, for example, a catalyst feed pipe which feeds a catalyst to the reaction tank 5 an inert gas feed pipe for substituting air for inert gas (e.g., nitrogen gas) in the reaction tank 5, and a stirrer for stirring in the reaction tank 5 may be provided as required in the reaction tank 5.

The amine feed pipe 6 is an amine feed line for feeding amine to the reaction tank 5, and the downstream end thereof is connected to the reaction tank 5. Though not shown, the upstream end thereof is connected to an amine introducing line for introducing amine.

The downstream end of an amine reflux pipe 30 (described later) is connected to the amine feed pipe 6 at a location in its flow direction. This enables the amine obtained in a residue decomposing tank 15 (described later) to be refluxed to the amine feed pipe 6 and then to be fed to the reaction tank 5.

The urea feed pipe 7 is a urea and/or N-unsubstituted carbamic acid ester feed line for feeding urea and/or N-unsubstituted carbamic acid ester to the reaction tank 5, and the downstream end thereof is connected to the reaction tank 5. Though not shown, the upstream end thereof is connected to a urea and/or N-unsubstituted carbamic acid ester introducing line for introducing urea and/or N-unsubstituted carbamic acid ester.

The alcohol feed pipe 8 is an alcohol feed line for feeding alcohol to the reaction tank 5, and the downstream end thereof is connected to the reaction tank 5. Though not shown, the upstream end thereof is connected to an alcohol introducing line for introducing alcohol.

The downstream end of an alcohol reflux pipe 32 (described later) is connected to the alcohol feed pipe 8 at a location in its flow direction. This enables the alcohol separated in a thermal decomposing tank 10 (described later) to be refluxed to the alcohol feed pipe 8 and then to be fed to the reaction tank 5.

The thermal decomposing system 3 is equipped in the plant 1, for the purpose of decomposing carbamates into isocyanate and alcohol while separating isocyanate residues from the decomposition solution.

The thermal decomposing system 3 includes a thermal decomposing tank 10, and a carbamate transporting pipe 11, a first solvent feed pipe 12, and an isocyanate drain pipe 13 which are connected to the thermal decomposing tank 10.

The thermal decomposing tank 10 is a decomposing tank for the carbamates obtained in the reaction system 2 to be decomposed into isocyanate and alcohol by heating. It comprises a heat-resistant and pressure-resistant vessel whose temperature and pressure can be controlled.

The carbamate transporting pipe 11 is a carbamate transporting line for transporting the carbamates produced in the reaction system 2 to the thermal decomposing tank 10, of which the downstream end is connected to the thermal decomposing tank 10 and the upstream end is connected to the reaction tank 5 in the reaction system 2.

The first solvent feed pipe 12 is a first solvent feed line for feeding a solvent to the thermal decomposing tank 10, and the downstream end thereof is connected to the thermal decomposing tank 10. Though not shown, the upstream end thereof is connected to a first solvent introducing line for introducing a solvent.

The downstream end of a solvent reflux pipe 31 (described later) is connected to the first solvent feed pipe 12 at a location in its flow direction. This enables the solvent, which is used in a residue decomposing tank 15 (described later) and is then recovered, to be refluxed to the first solvent feed pipe 12 and then to be fed to the thermal decomposing tank 10.

The isocyanate drain pipe 13 is an isocyanate drain line for draining the isocyanate obtained by the thermal decomposition of the carbamate out of the plant 1, and the upstream end thereof is connected to the thermal decomposing tank 10. Though not shown, the downstream end thereof is connected to an isocyanate purifying line for purifying the isocyanate.

The residue decomposing system 4 is equipped in the plant 1, for the purpose of decomposing the isocyanate residues obtained in the thermal decomposing system 3 into amine using high pressure and high temperature water.

The residue decomposing system 4 includes a residue decomposing tank 15, and an isocyanate residue transporting pipe 16, a second solvent feed pipe 17, a water feed pipe 18, and a secondary residue drain pipe 19 which are connected to the residue decomposing tank 15.

The residue decomposing tank 15 is a hydrolysis tank for hydrolyzing the isocyanate residues by contact with high pressure and high temperature water to give amine. It has a heat-resistant and pressure-resistant vessel whose temperature and pressure can be controlled.

Though not shown, for example, a water introducing pipe for filling the residue decomposing tank 15 with water (e.g., ion exchange water) and a stirrer for stirring in the residue decomposing tank 15 may be provided as required in the residue decomposing tank 15.

The isocyanate residue transporting pipe 16 is an isocyanate residue transporting line for transporting the isocyanate residues separated in the thermal decomposing system 3 to the residue decomposing tank 15, of which the downstream end is connected to the residue decomposing tank 15 and the upstream end is connected to the thermal decomposing tank 10 in the thermal decomposing system 3.

A residue pressure-feed pump (not shown) for pressure-transporting the isocyanate residues toward the residue decomposing tank 15 is interposed as required in the isocyanate residue transporting pipe 16. Further, a residue heater (not shown) for heating the isocyanate residues is interposed as required on the downstream side of the residue pressure-feed pump (not shown).

The second solvent feed pipe 17 is a second solvent feed line for feeding a solvent to the residue decomposing tank 15, and the downstream end thereof is connected to the residue decomposing tank 15. Though not shown, the upstream end thereof is connected to a second solvent introducing line for introducing a solvent.

A solvent pressure-feed pump (not shown) for pressure-transporting the solvent toward the residue decomposing tank 15 is interposed as required in the second solvent feed pipe 17. Further, a solvent heater (not shown) for heating the solvent is interposed as required on the downstream side of the solvent pressure-feed pump (not shown).

The water feed pipe 18 is a water feed line for feeding high pressure and high temperature water to the residue decomposing tank 15. It has a heat-resistant and pressure-resistant pipe of which the downstream end is connected to the residue decomposing tank 15 and the upstream end is connected to a water feed line for feeding water (recovered process water, ion-exchange water, etc.) not shown.

A water pressure-feed pump 21 for pressure-transporting the high pressure and high temperature water toward the residue decomposing tank 15 is interposed in the water feed pipe 18. A water heater 20 for heating water is further interposed in the water feed pipe 18 at a location on the downstream side of the water pressure-feed pump 21.

The secondary residue drain pipe 19 is a secondary residue drain line for draining components (secondary residues) which remain without being decomposed into amine, etc. when the isocyanate residues are brought into contact with high pressure and high temperature water, and the upstream end thereof is connected to the residue decomposing tank 15. Though not shown, the downstream end thereof is connected to a secondary residue storage tank for storing secondary residues.

The plant 1 further includes an amine reflux pipe 30, a solvent reflux pipe 31, and an alcohol reflux pipe 32.

The amine reflux pipe 30 is an amine reflux line for refluxing the amine, which has been obtained by decomposing the isocyanate residues in the residue decomposing system 4, to the amine feed pipe 6 in the reaction system 2, of which the upstream end is connected to the residue decomposing tank 15 and the downstream end is connected to a location in the flow direction of the amine feed pipe 6.

The solvent reflux pipe 31 is a solvent reflux line for refluxing the solvent, which has been used for the decomposition of the isocyanate residues in the residue decomposing system 4 and then recovered, to the first solvent feed pipe 12 in the thermal decomposing system 3, of which the upstream end is connected to the residue decomposing tank 15 and the downstream end is connected to a location in the flow direction of the first solvent feed pipe 12.

The alcohol reflux pipe 32 is an alcohol reflux line for refluxing the alcohol, which has been obtained by thermally decomposing the isocyanate in the thermal decomposing system 3, to the alcohol feed pipe 8 in the reaction system 2, of which the upstream end is connected to the thermal decomposing tank 10 and the downstream end is connected to a location in the flow direction of the alcohol feed pipe 8.

Next, a method for producing carbamate and isocyanate in the plant 1 followed by decomposition of the resulting isocyanate residues will be described below.

In this method, first, carbamates are produced in the reaction system 2.

In the production of the carbamate, the reaction system 2 is continuously operated to pressure-transport amine, urea and/or N-unsubstituted carbamic acid ester, and alcohol, which are a raw material for the carbamate, from the amine feed pipe 6, the urea feed pipe 7, and the alcohol feed pipe 8, respectively, at the above-mentioned proportion, thereby continuously feeding them to the reaction tank 5. In addition to these raw material components, a catalyst is fed from a catalyst feed pipe (not shown) as required.

In this method, the amine, urea and/or N-unsubstituted carbamic acid ester, and alcohol are subjected to carbamate formation reaction in the reaction tank 5, so that carbamates are produced.

The carbamate thus produced is separated in the reaction tank 5. Thereafter, the separated carbamate is fed to the carbamate transporting pipe 11 and is then pressure-transported to the thermal decomposing system 3.

Next, in this method, the carbamate is thermally decomposed in the thermal decomposing system 3.

In the thermal decomposition of the carbamate, while the thermal decomposing system 3 is continuously operated, the carbamate fed from the reaction system 2 (reaction tank 5) via the carbamate transporting pipe 11 is heated and thermally decomposed on the above conditions in the thermal decomposing tank 10.

Thus, a decomposition solution including isocyanate and alcohol is obtained, and the isocyanate and the alcohol are separated from the decomposition solution to thereby obtain isocyanate residues.

On the other hand, the alcohol obtained in the thermal decomposing tank 10 is separated from the decomposition solution. Thereafter, the separated alcohol is introduced into the alcohol reflux pipe 32 and then refluxed to the alcohol feed pipe 8. As a result, the alcohol is fed to the reaction tank 5.

The isocyanate residues obtained in the thermal decomposing tank 10 is fed to the isocyanate residue transporting pipe 16 and is then pressure-transported to the residue decomposing system 4.

Next, in this method, the isocyanate residues are decomposed in the residue decomposing system 4.

In the decomposition of the isocyanate residues, while the residue decomposing system 4 is continuously operated, the isocyanate residues fed from the thermal decomposing system 3 (thermal decomposing tank 10) via the isocyanate residue transporting pipe 16 are decomposed on the above conditions in the residue decomposing tank 15.

Specifically, in this method, the isocyanate residues are fed to the residue decomposing tank 15 via the isocyanate residue transporting pipe 16 in the state of being increased in pressure to a feeding pressure of, for example, 3 to 30 MPa and being heated to a feeding temperature of for example, 190 to 350° C.

A solvent is also fed to the residue decomposing tank 15 via the second solvent feed pipe 17 in the state of being increased in pressure to a feeding pressure of, for example, 3 to 30 MPa and being heated to a feeding temperature of, for example, 190 to 350° C.

On the other hand, water flowing into the water feed pipe 18 from the water feed line is pressure-transported through the water feed pipe 18 by the water pressure-feed pump 21, flowing toward the residue decomposing tank 15, during which the water is heated to, for example, 190 to 350° C. by the water heater 20. As a result, the water is increased in pressure to 3 to 30 MPa as well as in temperature to 190 to 350° C., thereby to become a high pressure and high temperature water. Then, the high pressure and high temperature water is flown into the residue decomposing tank 15.

The residue decomposing tank 15 is controlled to an inner temperature (decomposing temperature) of, for example, 190 to 350° C. and an inner pressure (decomposing pressure) of, for example, 3 to 30 MPa. Further, a hydrolytic ratio (a mass ratio of (high pressure and high temperature water/polyisocyanate residues)) is controlled to, for example, 0.5 to 10 under control of the residue pressure-feed pump (not shown) and the water pressure-feed pump 21.

As a result of this, in the residue decomposing tank 15, the isocyanate residues are hydrolyzed with the high pressure and high temperature water to produce a corresponding amine as a decomposition product, during which secondary residues, carbon dioxide, and water are by-produced.

The decomposition products obtained in the residue decomposing tank 15 are reduced in pressure to the atmospheric pressure and are subsequently separated to each in a dehydrating column, though not shown, so that amine is recovered.

The amine thus recovered is introduced into the amine reflux pipe 30 and then refluxed to the amine feed pipe 6. As a result, the amine is fed to the reaction tank 5.

Further, the solvent used in the residue decomposing tank 15 is recovered by a known method. Thereafter, the recovered solvent is introduced into the solvent reflux pipe 31 and refluxed to the first solvent feed pipe 12. As a result, the solvent is fed to the thermal decomposing tank 10.

The secondary residues obtained in the residue decomposing tank 15 are transported to the secondary residue storage tank (not shown) via the secondary residue drain pipe 19 and then temporarily stored in the secondary residue storage tank (not shown). Thereafter, the stored secondary residues are incinerated, for example.

The plant 1 can include a known processing system such as a distillation system, a filtration system, or a purification system, in an appropriate position as required.

With the plant 1, carbamate and isocyanate are continuously produced while isocyanate residues are decomposed, and the amine obtained by decomposition of the isocyanate residues, the solvent used for the decomposition, and the alcohol by-produced in the production of the isocyanate are refluxed, so that they can be efficiently used.

In the above description, the isocyanate residues are hydrolyzed by contact with high pressure and high temperature water in the presence of the solvent to give amine and alcohol. However, carbonate may be blended with the isocyanate residues, so that the blended isocyanate residues are hydrolyzed by contact with high pressure and high temperature water to give amine and alcohol.

Specifically, the isocyanate residues are often in the form of a high viscosity tar. From the industrial view point, however, it is desirable to prepare the isocyanate residues in slurry form by imparting fluidity thereto for slurry transportation. Therefore, carbonate is blended with the isocyanate residues in the following method.

Examples of the carbonate include dialkyl carbonate, diaryl carbonate, and alkyl aryl carbonate.

The dialkyl carbonate is represented, for example, by the following general formula (11):

$$R^3OCOOR^4 \tag{11}$$

(wherein $R^3$ and $R^4$ may be the same or different from each other, and each represents an alkyl group.)

Examples of the alkyl group represented by $R^3$ and $R^4$ in formula (11) above include the above-mentioned alkyl groups (the alkyl group in formula (2) above).

More specifically, examples of the dialkyl carbonate include symmetrical dialkyl carbonate such as dimethyl carbonate, diethyl carbonate, di(n-)propyl carbonate, di(n-)butyl carbonate, dicyclohexyl carbonate, and dicyclododecyl carbonate; and asymmetrical dialkyl carbonate such as methylethyl carbonate, methyl(n-)propyl carbonate, ethyl(n-)propyl carbonate, methylcyclohexyl carbonate, and cyclohexyl cyclododecyl carbonate.

The diaryl carbonate is represented, for example, by the following general formula (12):

$$R^5OCOOR^6 \tag{12}$$

(wherein $R^5$ and $R^6$ may be the same or different from each other and each represents an aryl group which may have a substituent.)

In formula (12) above, examples of the aryl group which may have a substituent represented by $R^5$ and $R^6$ include the above-mentioned aryl groups which may have a substituent (the aryl groups which may have a substituent in formula (2) above).

More specifically, examples of the diaryl carbonate include symmetrical diaryl carbonate such as diphenyl carbonate, ditolyl carbonate, and dixylyl carbonate; and asymmetrical diaryl carbonate such as phenyl tolyl carbonate and phenyl xylyl carbonate.

The alkyl aryl carbonate is represented, for example, by the following general formula (13):

$$R^7OCOOR^8 \tag{13}$$

(wherein $R^7$ represents an alkyl group, and $R^8$ represents an aryl group which may have a substituent.)

In formula (13) above, examples of the alkyl group represented by $R^7$ include the above-mentioned alkyl groups (alkyl group in formula (2) above).

In formula (13) above, examples of the aryl group which may have a substituent represented by $R^8$ include the above-mentioned aryl groups which may have a substituent (the aryl groups which may have a substituent in formula (2) above).

More specifically, examples of the alkyl aryl carbonate include methyl phenyl carbonate, ethyl phenyl carbonate, methyl tolyl carbonate, and methyl xylyl carbonate.

These carbonates can be used alone or in combination of two or more kinds.

As the carbonate, dialkyl carbonate is preferable.

The carbonate can be produced by a known method, or a commercially available carbonate may be used.

In addition, for example, there may be used the carbonate (formula (7) above) obtained as a by-product in the reaction (carbamate formation reaction) in which amine, urea and/or N-unsubstituted carbamic acid ester, and alcohol are allowed to react to thereby obtain carbamates as described above.

Preferably, the carbonate obtained as a by-product in the carbamate formation reaction of urea and/or N-unsubstituted carbamic acid ester, and an alcohol is used.

More specifically, when the alcohol (excess (unreacted) alcohol and by-produced alcohol (formula (5) above)), the N-unsubstituted carbamic acid ester, and the carbonate each are further roughly separated by distillation, etc. from the low boiling components (light-boiling fractions) separated from the reaction solution obtained by the above-mentioned carbamate formation reaction, the alcohol, the N-unsubstituted carbamic acid ester, and the carbonate each can be roughly separated and recovered.

Then, in this method, the alcohol (excess (unreacted) alcohol and by-produced alcohol) roughly separated from the low boiling components (light-boiling fractions) is used as a raw material component for the carbamate formation reaction.

Therefore, the alcohol roughly separated from the low boiling components (light-boiling fractions) can be industrially effectively used.

The N-unsubstituted carbamic acid ester roughly separated from the low boiling components (light-boiling fractions) is also used as a raw material component for the carbamate formation reaction.

Therefore, the N-unsubstituted carbamic acid ester roughly separated from the low boiling components (light-boiling fractions) can be industrially effectively used.

In this method, the carbonate roughly separated from the low boiling components (light-boiling fractions) is blended with the isocyanate residues.

Effective use of carbonate can be achieved by using the carbonate obtained as a by-product in the carbamate formation reaction.

In this method, the isocyanate residues blended with the carbonate (and a solvent as required) are fed into a known pressure-resistant and heat-resistant tank while high pressure and high temperature water is fed thereinto, and the isocyanate residues are hydrolyzed by contact with high pressure and high temperature water to give amine and alcohol.

The high pressure and high temperature water is water which is increased in pressure to a high pressure, that is, from 3 to 30 MPa, preferably from 6 to 25 MPa, or more preferably from 6 to 20 MPa, as well as in temperature to a high temperature, that is, from 190 to 350° C., or preferably from 200 to 300° C., and is heated and pressurized by a known method.

The decomposing pressure (inner pressure) of the isocyanate residues (containing the carbonate) is in the range of 3 to 30 MPa, preferably 6 to 25 MPa, or more preferably 6 to 20 MPa. The decomposing temperature (inner temperature) of the isocyanate residues (containing the carbonate) is in the range of 190 to 350° C., or preferably 200 to 300° C.

As the high pressure and high temperature water, a hydrolytic ratio (a mass ratio of (high pressure and high temperature water/isocyanate residues (containing the carbonate))) is controlled to, for example, 0.5 to 30, or preferably 1 to 15.

As a result of this, the isocyanate residues are hydrolyzed with the high pressure and high temperature water to produce amine as a decomposition product, while the carbonate blended with the isocyanate residues is hydrolyzed with the high pressure and high temperature water to produce alcohol as a decomposition product. In such hydrolysis, carbon dioxide, etc. are also by-produced.

At this time, when the isocyanate residues to be hydrolyzed are those obtained by thermally decomposing the carbamate produced by the reaction of amine, urea and/or N-unsubstituted carbamic acid ester, and alcohol as described above, an amine represented by general formula (10) above is produced as the corresponding amine.

$$R^1\text{—}(NH_2)n \qquad (10)$$

(wherein $R^1$ is defined as $R^1$ in formula (1) above, and n is defined as n in formula (1) above.)

In other words, when the isocyanate residues obtained by separating isocyanate and alcohol from the decomposition solution, which has been obtained by the thermal decomposition reaction of the carbamate, are decomposed, the same type of amine (general formula (10) above) as the amine (general formula (1) above) used for the production of the carbamate and the isocyanate is obtained. Such amine obtained by decomposing the isocyanate residues is, after separated and recovered, preferably used as raw material amine (general formula (1) above) during the production of the carbamate described above.

A known method may be used to separate the amine, and distillation is preferable.

At this time, when the carbonate blended with the isocyanate residues is the carbonate (formula (7) above) obtained as a by-product in the carbamate formation reaction, an alcohol represented by the following general formula (14) is produced as the corresponding alcohol:

$$R^2\text{—OH} \qquad (14)$$

(wherein $R^2$ is defined as $R^2$ in formula (2) above.)

That is, the carbonate roughly separated from the low boiling components (light-boiling fractions) is blended with the isocyanate residues, whereby the same alcohol as the alcohol represented by formula (3) above is produced.

In the rough separation of the low boiling components (light-boiling fractions), N-unsubstituted carbamic acid ester may be contained in the carbonate. Even in such case, the carbonate and the N-unsubstituted carbamic acid ester can be decomposed into alcohol at once by contact with high pressure and high temperature water.

In this method, the alcohol (formula (14) above) obtained by decomposing the carbonate is preferably used as the raw material component for the carbamate formation reaction.

Therefore, the alcohol obtained by decomposing the carbonate roughly separated from the low boiling components is used as the raw material component for the carbamate formation reaction, whereby the carbonate by-produced in the carbamate formation reaction can be industrially effectively used.

According to the method for treating isocyanate residues of the present invention, since carbonate is blended with the isocyanate residues obtained from the carbamate decomposition solution and the blended mixture is then hydrolyzed, amine and alcohol can be obtained at once.

Therefore, according to the method for treating isocyanate residues of the present invention, the isocyanate residues and the carbonate can be industrially effectively used.

Figure 2:
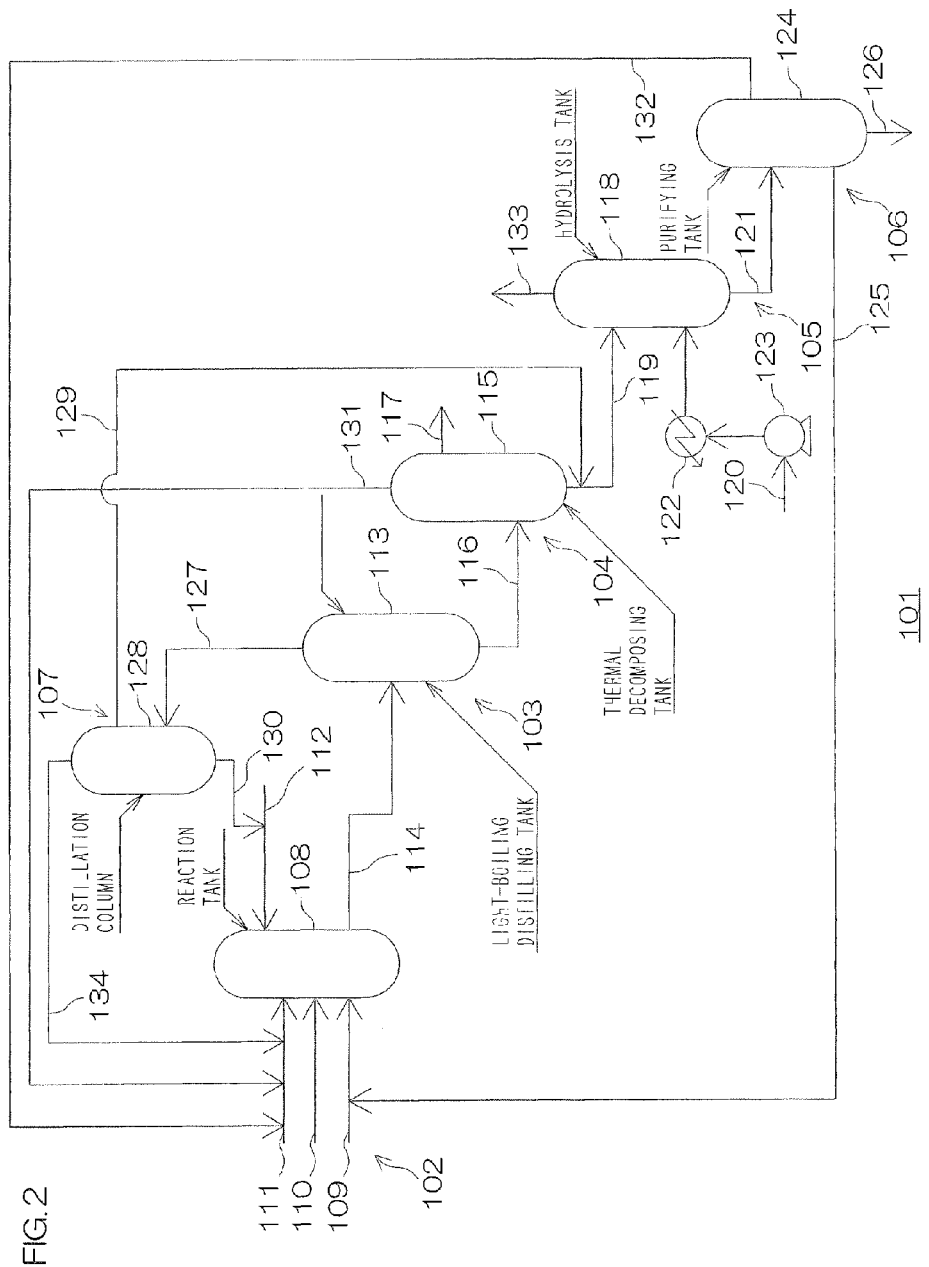
FIG. 2 is a schematic configuration diagram showing another embodiment of a plant employing a method for treating isocyanate residues according to the present invention.

FIG. 2 is a schematic configuration diagram showing another embodiment of a plant employing a method for treating isocyanate residues according to the present invention.

Another embodiment of the plant where the above-mentioned method for treating isocyanate residues is industrially carried out is described below with reference to FIG. 2.

In FIG. 2, this plant 101 is an isocyanate production system which produces an isocyanate by a urea method during which isocyanate residues are obtained, and applies the above-mentioned method for treating isocyanate residues to the isocyanate residues, and includes a reaction system 102, a light-boiling distillation system 103, a thermal decomposing system 104, a distillation system 107, a hydrolysis system 105, and a purification system 106.

The reaction system 102 is equipped in the plant 101, for the purpose of producing carbamates by reaction of amine, urea and/or N-unsubstituted carbamic acid ester, and alcohol.

The reaction system 102 includes a reaction tank 108, and an amine feed pipe 109, a urea feed pipe 110, a carbamic acid ester feed pipe 112, and an alcohol feed pipe 111 which are connected to the reaction tank 108.

The reaction tank 108 is a carbamate formation reaction tank for carbamates to be produced by carbamate formation reaction of amine, urea and/or N-unsubstituted carbamic acid ester, and alcohol. It has a heat-resistant and pressure-resistant vessel whose temperature and pressure can be controlled.

Though not shown, for example, a catalyst feed pipe which feeds a catalyst to the reaction tank 108, an inert gas feed pipe for substituting air for inert gas (e.g., nitrogen gas) in the reaction tank 108, a stirrer for stirring in the reaction tank 108, and an ammonia drain pipe which distills by-produced ammonia out of the system may be provided as required in the reaction tank 108.

The amine feed pipe 109 is an amine feed line for feeding amine to the reaction tank 108, and the downstream end thereof is connected to the reaction tank 108. Though not shown, the upstream end thereof is connected to an amine introducing line for introducing amine.

The downstream end of an amine reflux pipe 125 (described later) is connected to the amine feed pipe 109 at a location in its flow direction.

The urea feed pipe 110 is a urea feed line for feeding urea to the reaction tank 108, and the downstream end thereof is connected to the reaction tank 108. Though not shown, the upstream end thereof is connected to a urea introducing line for introducing urea.

The carbamic acid ester feed pipe 112 is an N-unsubstituted carbamic acid ester feed line for feeding N-unsubstituted carbamic acid ester to the reaction tank 108, and the downstream end thereof is connected to the reaction tank 108. Though not shown, the upstream end thereof is connected to an N-unsubstituted carbamic acid ester introducing line for introducing N-unsubstituted carbamic acid ester.

The downstream end of a carbamic acid ester reflux pipe 130 (described later) is connected to the carbamic acid ester feed pipe 112 at a location in its flow direction.

The alcohol feed pipe 111 is an alcohol feed line for feeding alcohol to the reaction tank 108, and the downstream end thereof is connected to the reaction tank 108. Though not shown, the upstream end thereof is connected to an alcohol introducing line for introducing alcohol.

The downstream end of a first alcohol reflux pipe 131 (described later), the downstream end of a second alcohol reflux pipe 132 (described later), and the downstream end of a third alcohol reflux pipe 134 are connected to the alcohol feed pipe 111 at locations in their flow directions.

The light-boiling distillation system 103 is equipped in the plant 101, for the purpose of separating low boiling components (light-boiling fractions) such as excess (unreacted) alcohol, urea and/or N-unsubstituted carbamic acid ester; and alcohol, N-unsubstituted carbamic acid ester, and carbonate which are by-products, from the reaction solution obtained in the reaction tank 108.

The light-boiling distillation system 103 includes a light-boiling distilling tank 113 and a first reaction-solution transporting pipe 114 connected to the light-boiling distilling tank 113.

The light-boiling distilling tank 113 is a distilling tank for distilling off the above-mentioned low boiling components from the reaction solution obtained in the reaction system 102. It has a heat-resistant and pressure-resistant vessel whose temperature and pressure can be controlled.

The first reaction-solution transporting pipe 114 is a first reaction-solution transporting line for transporting the reaction solution produced in the reaction system 102 to the light-boiling distilling tank 113, of which the downstream end is connected to the light-boiling distilling tank 113 and the upstream end is connected to the reaction tank 108 in the reaction system 102.

The thermal decomposing system 104 is equipped in the plant 101, for the purpose of thermally decomposing the reaction solution into isocyanate and alcohol.

The thermal decomposing system 104 include a thermal decomposing tank 115, and a second reaction-solution transporting pipe 116 and an isocyanate drain pipe 117 which are connected to the thermal decomposing tank 115.

The thermal decomposing tank 115 is a decomposing tank for the reaction solution obtained in the reaction system 102 to be thermally decomposed into isocyanate and alcohol by heating. It has a heat-resistant and pressure-resistant vessel whose temperature and pressure can be controlled.

Though not shown, for example, a solvent feed pipe which feeds a solvent to the thermal decomposing tank 115 may be provided as required in the thermal decomposing tank 115.

The second reaction-solution transporting pipe 116 is a second reaction-solution transporting line for transporting the reaction solution in which the light-boiling fractions have been distilled off in the light-boiling distillation system 103, to the thermal decomposing tank 115, of which the downstream end is connected to the thermal decomposing tank 115 and the upstream end is connected to the light-boiling distilling tank 113 in the light-boiling distillation system 103.

The isocyanate drain pipe 117 is an isocyanate drain line for draining the isocyanate obtained by the thermal decomposition of the reaction solution out of the plant 101, and the upstream end thereof is connected to the thermal decomposing tank 115. Though not shown, the downstream end thereof is connected to an isocyanate purifying line for purifying the isocyanate.

The distillation system 107 is equipped in the plant 101, for the purpose of separating alcohol, N-unsubstituted carbamic acid ester, and carbonate from the low boiling components (light-boiling fractions) obtained in the light-boiling distilling tank 113.

The distillation system 107 includes a distillation column 128 and a light-boiling fraction transporting pipe 127 connected to the distillation column 128.

The distillation column 128 is a separation column for roughly separating the N-unsubstituted carbamic acid ester as well as the carbonate, and further roughly separating the alcohol from the low boiling components obtained in the light-boiling distillation system 103. It has a known distillation column.

The light-boiling fraction transporting pipe 127 is a light-boiling fraction transporting line for transporting the light-boiling fractions obtained in the light-boiling distillation system 103 to the distillation system 107, of which the downstream end is connected to the distillation column 128 and the upstream end is connected to the light-boiling distilling tank 113 in the light-boiling distillation system 103.

The hydrolysis system 105 is equipped in the plant 101, for the purpose of blending the carbonate obtained in the distillation system 107 with the isocyanate residues obtained in the thermal decomposing system 104 and hydrolyzing the carbonate-blended isocyanate residues with high pressure and high temperature water to give amine and alcohol.

The hydrolysis system 105 includes a hydrolysis tank 118, an isocyanate residue transporting pipe 119 and a water feed pipe 120 which are connected to the hydrolysis tank 118, and a carbonate transporting pipe 129 connected to the isocyanate residue transporting pipe 119.

The hydrolysis tank 118 is a hydrolysis tank for hydrolyzing the isocyanate residues (containing the carbonate) by contact of the carbonate-blended isocyanate residues with high pressure and high temperature water to give amine and alcohol, so that a hydrolyzed solution is obtained. It has a heat-resistant and pressure-resistant vessel whose temperature and pressure can be controlled.

A drain pipe 133 which drains the carbon dioxide by-produced by the hydrolysis of the isocyanate residues (containing the carbonate) and the water or the like used for the hydrolysis from the plant 101 is provided in the hydrolysis tank 118.

Though not shown, for example, a stirrer for stirring in the hydrolysis tank 118 may be provided in the hydrolysis tank 118 as required.

The isocyanate residue transporting pipe 119 is an isocyanate residue transporting line for transporting the isocyanate residues produced in the thermal decomposing system 104 to the hydrolysis tank 118, of which the downstream end is connected to the hydrolysis tank 118 and the upstream end is connected to the thermal decomposing tank 115 in the thermal decomposing system 104.

The downstream end of the carbonate transporting pipe 129 is connected to the isocyanate residue transporting pipe 119 at a location in its flow direction.

In the isocyanate residue transporting pipe 119, a residue pressure-feed pump (not shown) for pressure-transporting the isocyanate residues (containing the carbonate) toward the hydrolysis tank 118 is interposed as required at a location on the downstream side where the carbonate transporting pipe 129 is connected. Further, a residue heater (not shown) for heating the isocyanate residues (containing the carbonate) is interposed as required on the downstream side of the residue pressure-feed pump (not shown).

The water feed pipe 120 is a water feed line for feeding high pressure and high temperature water to the hydrolysis tank 118. It has a heat-resistant and pressure-resistant pipe of which the downstream end is connected to the hydrolysis tank 118 and the upstream end is connected to a water feed line for feeding water (recovered process water, ion-exchange water, etc.) not shown.

A water pressure-feed pump 123 for pressure-transporting the high pressure and high temperature water toward the hydrolysis tank 118 is interposed in the water feed pipe 120. A water heater 122 for heating water is further interposed in the water feed pipe 120 at a location on the downstream side of the water pressure-feed pump 123.

The carbonate transporting pipe 129 is a carbonate transporting line for transporting the carbonate recovered in the distillation system 107 to the hydrolysis system 105, of which the upstream end is connected to the distillation column 128 and the downstream end is connected to a location in the flow direction of the isocyanate residue transporting pipe 119 in the hydrolysis system 105.

A carbonate pressure-feed pump (not shown) for pressure-transporting the carbonate toward the isocyanate residue transporting pipe 119 is interposed as required in the carbonate transporting pipe 129. Further, a carbonate heater (not shown) for heating the carbonate is interposed as required on the downstream side of the carbonate pressure-feed pump (not shown).

The purification system 106 is equipped in the plant 101, for the purpose of separating and purifying the amine and the alcohol from the hydrolyzed solution containing the amine and the alcohol obtained in the hydrolysis tank 118, and further containing the components (secondary residues) which remain without being decomposed into amine, alcohol, etc.

The purification system 106 includes a purifying tank 124, and a hydrolyzed solution transporting pipe 121 and a secondary residue drain pipe 126 which are connected to the purifying tank 124.

The purifying tank 124 is a purifying tank for separating and purifying the amine and the alcohol from the hydrolyzed solution obtained in the hydrolysis system 105. It has a heat-resistant and pressure-resistant vessel whose temperature and pressure can be controlled.

The hydrolyzed solution transporting pipe 121 is a hydrolyzed solution transporting line for transporting the reaction solution produced in the hydrolysis system 105 to the purifying tank 124, of which the downstream end is connected to the purifying tank 124 and the upstream end is connected to the hydrolysis tank 118 in the hydrolysis system 105.

The secondary residue drain pipe 126 is a secondary residue drain line for draining components (secondary residues) which remain without being decomposed into amine, alcohol, etc. when the isocyanate residues (carbonate) are brought into contact with high pressure and high temperature water, and the upstream end thereof is connected to the purifying tank 124. Though not shown, the downstream end thereof is connected to a secondary residue storage tank for storing secondary residues.

The plant 101 further includes an amine reflux pipe 125, a first alcohol reflux pipe 131, a second alcohol reflux pipe 132, a third alcohol reflux pipe 134, and a carbamic acid ester reflux pipe 130.

The amine reflux pipe 125 is an amine reflux line for refluxing the amine, which has been separated from the hydrolyzed solution and then purified in the purification system 106, to the amine feed pipe 109 in the reaction system 102, of which the upstream end is connected to the purifying tank 124 and the downstream end thereof is connected to a location in the flow direction of the amine feed pipe 109.

The first alcohol reflux pipe 131 is a first alcohol reflux line for refluxing the alcohol, which has been obtained by thermally decomposing the isocyanate in the thermal decomposing system 104, to the alcohol feed pipe 111 in the reaction system 102, of which the upstream end is connected to the thermal decomposing tank 115 and the downstream end is connected to a location in the flow direction of the alcohol feed pipe 111.

The second alcohol reflux pipe 132 is a second alcohol reflux line for refluxing the alcohol, which has been separated from the hydrolyzed solution and then purified in the purification system 106, to the alcohol feed pipe 111 in the reaction system 102, of which the upstream end is connected to the purifying tank 124 and the downstream end is connected to a location in the flow direction of the alcohol feed pipe 111.

The third alcohol reflux pipe 134 is a third alcohol reflux line for refluxing the alcohol, which has been obtained by distilling the low boiling components (light-boiling fractions) in the distillation system 107, to the alcohol feed pipe 111 in the reaction system 102, of which the upstream end is connected to the distillation column 128 and the downstream end is connected to a location in the flow direction of the alcohol feed pipe 111.

The carbamic acid ester reflux pipe 130 is a carbamic acid ester reflux line for refluxing the N-unsubstituted carbamic acid ester, which has been obtained by distilling the low boiling components (light-boiling fractions) in the distillation system 107, to the carbamic acid ester feed pipe 112 in the reaction system 102, of which the upstream end is connected to the distillation column 128 and the downstream end is connected to a location in the flow direction of the carbamic acid ester feed pipe 112.

Next, the following method will be described below: carbamates and isocyanates are produced in the plant 101 as well as obtaining isocyanate residues, while carbonate is obtained from the low boiling components obtained in the production of the carbamate, the carbonate is blended with the isocyanate residues, and the resulting isocyanate residues (containing the carbonate) are hydrolyzed to give amine and alcohol, so that the resulting amine and alcohol are used again as raw material components for the carbamate formation reaction.

In this method, first, carbamate is produced in the reaction system 102.

In the production of the carbamate, the reaction system 102 is continuously operated to pressure-transport amine, urea and/or N-unsubstituted carbamic acid ester, and alcohol, which are a raw material for the carbamate, from the amine feed pipe 109, the urea feed pipe 110 and/or the carbamic acid ester feed pipe 112, and the alcohol feed pipe 111, respectively, at the above-mentioned proportion, thereby continuously feeding them to the reaction tank 108. In addition to these raw material components, a catalyst is fed from a catalyst feed pipe (not shown) as required.

In this method, the amine, urea and/or N-unsubstituted carbamic acid ester, and alcohol are subjected to carbamate formation reaction in the reaction tank 108, so that a reaction solution containing carbamate, and alcohol, N-unsubstituted carbamic acid ester and carbonate which are by-produced is obtained.

The reaction solution thus obtained is fed to the first reaction-solution transporting pipe 114 and is then pressure-transported to the light-boiling distillation system 103.

Next, in this method, low boiling components (light-boiling fractions) such as excess (unreacted) alcohol, urea and/or N-unsubstituted carbamic acid ester; and alcohol, N-unsubstituted carbamic acid ester, and carbonate which are by-products, are separated from the reaction solution in the light-boiling distillation system 103 (light-boiling distilling tank 113).

The light-boiling fractions separated in the light-boiling distilling tank 113 are introduced into the light-boiling fraction transporting pipe 127 and then fed to the distillation system 107.

In this method, the low boiling components (light-boiling fractions) fed to the distillation system 107 are distilled in the distillation column 128, to thereby roughly separate the N-unsubstituted carbamic acid ester, the carbonate, and the alcohol (containing excess (unreacted) alcohol and by-produced alcohol).

The N-unsubstituted carbamic acid ester thus roughly separated is introduced into the carbamic acid ester reflux pipe 130, and then refluxed to the carbamic acid ester feed pipe 112. As a result, the N-unsubstituted carbamic acid ester is fed to the reaction tank 108.

Also, the alcohol thus roughly separated is introduced into the third alcohol reflux pipe 134 and then refluxed to the alcohol feed pipe 111. As a result, the alcohol is fed to the reaction tank 108.

The carbonate (which may contain the N-unsubstituted carbamic acid ester in some cases) is fed to the carbonate transporting pipe 129 and then pressure-transported to a location in the flow direction of the isocyanate residue transporting pipe 119.

On the other hand, in the light-boiling distillation system 103, the reaction solution obtained as a residue after the light-boiling fractions are separated from the reaction solution is fed to the second reaction-solution transporting pipe 116 and then pressure-transported to the thermal decomposing system 104.

Next, in this method, the reaction solution is thermally decomposed in the thermal decomposing system 104.

In the thermal decomposition of the reaction solution, while the thermal decomposing system 104 is continuously operated, the reaction solution fed via the second reaction-solution transporting pipe 116 is heated and thermally decomposed on the above conditions in the thermal decomposing tank 115.

Thus, a decomposition solution including isocyanate and alcohol is obtained, and isocyanate residues are also obtained as well as the isocyanate and the alcohol.

The isocyanate obtained in the thermal decomposing tank 115 is drained via the isocyanate drain pipe 117 and then transported to the isocyanate purifying line which is not shown.

On the other hand, the alcohol obtained in the thermal decomposing tank 115 is introduced into the first alcohol reflux pipe 131 after separated from the decomposition solution, and then refluxed to the alcohol feed pipe 111. As a result, the alcohol is fed to the reaction tank 108.

The isocyanate residues obtained in the thermal decomposing tank 115 are fed to the isocyanate residue transporting pipe 119, and then pressure-transported to the hydrolysis system 105.

At this time, the carbonate transported from the distillation column 128 via the carbonate transporting pipe 129 is blended with the isocyanate residues in the isocyanate residue transporting pipe 119.

Such blending with the carbonate converts the form of the isocyanate residues from the high viscosity tar to slurry, which ensures fluidity. Therefore, the resulting isocyanate residues in the slurry form are efficiently pressure-transported to the hydrolysis system 105.

Next, in this method, the isocyanate residues blended with the carbonate are hydrolyzed in the hydrolysis system 105.

In the hydrolysis of the isocyanate residues, while the hydrolysis system 105 is continuously operated, the isocyanate residues (containing the carbonate) fed from the thermal decomposing system 104 (thermal decomposing tank 115) via the isocyanate residue transporting pipe 119 are decomposed on the above conditions in the hydrolysis tank 118.

Specifically, in this method, the isocyanate residues (containing the carbonate) are fed to the hydrolysis tank 118 via the isocyanate residue transporting pipe 119 in the state of being increased in pressure to a feeding pressure of for example, 3 to 30 MPa and being heated to a feeding temperature of for example, 190 to 350° C.

On the other hand, the water flowing into the water feed pipe 120 from the water feed line is pressure-transported through the water feed pipe 120 by the water pressure-feed pump 123, flowing toward the hydrolysis tank 118, during which the water is heated by the water heater 122. As a result, the water is increased in pressure to 3 to 30 MPa as well as in temperature to 190 to 350° C. thereby to become a high pressure and high temperature water. Then, the high pressure and high temperature water is flown into the hydrolysis tank 118.

The hydrolysis tank 118 is controlled to an inner temperature (decomposing temperature) of, for example, 190 to 350° C. and an inner pressure (decomposing pressure) of, for example, 3 to 30 MPa. Further, a hydrolytic ratio (a mass ratio of (high pressure and high temperature water/isocyanate residues (containing the carbonate)) is controlled to, for example, 0.5 to 30 under control of the residue pressure-feed pump (not shown) and the water pressure-feed pump 123.

As a result of this, in the hydrolysis tank 118, the isocyanate residues (containing the carbonate) are continuously hydrolyzed with the high pressure and high temperature water to produce corresponding amine and alcohol as decomposition products, so that a hydrolyzed solution containing the amine and the alcohol, and further containing components (secondary residues) which remain unhydrolyzed is obtained.

The by-produced carbon dioxide and the water used for the hydrolysis are drained from the plant 101 via the drain pipe 133.

The hydrolyzed solution containing the amine and the alcohol, and further containing secondary residues is fed to the hydrolyzed solution transporting pipe 121, and then pressure-transported to the purification system 106.

Next, in this method, the amine and the alcohol are separated from the hydrolyzed solution in the purification system 106 (purification tank 124).

The amine thus separated is introduced into the amine reflux pipe 125 and then refluxed to the amine feed pipe 109. As a result, the amine is fed to the reaction tank 108.

The alcohol thus separated is also introduced into the second alcohol reflux pipe 132 and then refluxed to the alcohol feed pipe 111. As a result, the alcohol is fed to the reaction tank 108.

The secondary residues obtained in the purification tank 124 are transported to the secondary residue storage tank (not shown) via the secondary residue drain pipe 126 and then temporarily stored in the secondary residue storage tank (not shown). Thereafter, the stored secondary residues are incinerated, for example.

With the plant 101, isocyanate is continuously produced while the amine and alcohol obtained by decomposing at once the isocyanate residues and the carbonate which is obtained as a by-product of the carbamate formation reaction are refluxed, so that they can be efficiently used.

Further, with the plant 101, the alcohol and the N-unsubstituted carbamic acid ester obtained as by-products of the carbamate formation reaction are separated, and the alcohol and the N-unsubstituted carbamic acid ester thus separated are then refluxed, so that they can be efficiently used.

In the foregoing, the method for treating isocyanate residues has been discussed. However, the plants in FIGS. 1 and 2 can include a pre-treatment system for carrying out pre-treatment steps including a dehydration step, and a post-treatment system for carrying out post-treatment steps including intermediate steps, a distillation step, a filtration step, a purification step, and a recovery step, in appropriate positions as required.

According to the method for treating carbonates of the present invention, the carbonate is decomposed into alcohol by contact with high pressure and high temperature water.

As the carbonate, at least one kind selected from the group consisting of dialkyl carbonate, diaryl carbonate, and alkyl aryl carbonate is used.

The dialkyl carbonate is represented, for example, by the following general formula (15):

$$R^{11}OCOOR^{12} \tag{15}$$

(wherein $R^{11}$ and $R^{12}$ may be the same or different from each other and each represents an alkyl group.)

In formula (15) above, examples of the alkyl group represented by $R^{11}$ and $R^{12}$ include a linear or branched saturated hydrocarbon group having 1 to 8 carbon atoms such as methyl, ethyl, n-propyl, iso-propyl, n-butyl, iso-butyl, sec-butyl, tert-butyl, pentyl, hexyl, heptyl, octyl, iso-octyl, and 2-ethylhexyl; and an alicyclic saturated hydrocarbon group having 5 to 10 carbon atoms such as cyclohexyl and cyclododecyl.

More specifically, examples of the dialkyl carbonate include symmetrical dialkyl carbonate such as dimethyl carbonate, diethyl carbonate, di(n-)propyl carbonate, di(n-)butyl carbonate, dicyclohexyl carbonate, and dicyclododecyl carbonate; and asymmetrical dialkyl carbonate such as methylethyl carbonate, methyl(n-)propyl carbonate, ethyl(n-)propyl carbonate, methylcyclohexyl carbonate, and cyclohexyl cyclododecyl carbonate.

The diaryl carbonate is represented, for example, by the following general formula (16):

$$R^{13}OCOOR^{14} \tag{16}$$

(wherein $R^{13}$ and $R^{14}$ may be the same or different from each other and each represents an aryl group which may have a substituent.)

In formula (16) above, examples of the aryl group which may have a substituent represented by $R^{13}$ and $R^{14}$ include aryl groups having 6 to 18 carbon atoms such as phenyl, tolyl, xylyl, biphenyl, naphthyl, anthryl, and phenanthryl. Further, examples of the substituent include a hydroxyl group, a halogen atom (e.g., chlorine, fluorine, bromine, and iodine), a cyano group, an amino group, a carboxyl group, an alkoxy group (e.g., an alkoxy group having 1 to 4 carbon atoms such as a methoxy, an ethoxy, a propoxy, or a butoxy group), an aryloxy group (e.g., a phenoxy group), an alkylthio group (e.g., an alkylthio group having 1 to 4 carbon atoms such as a methylthio, an ethylthio, a propylthio, or a butylthio group), and an arylthio group (e.g., phenylthio group). When the substituents are multiply substituted at the aryl group, the substituents may be the same or different from each other.

More specifically, examples of the diaryl carbonate include symmetrical diaryl carbonate such as diphenyl carbonate, ditolyl carbonate, and dixylyl carbonate; and asymmetrical diaryl carbonate such as phenyl tolyl carbonate and phenyl xylyl carbonate.

The alkyl aryl carbonate is represented, for example, by the following general formula (17):

$$R^{15}OCOOR^{16} \tag{17}$$

(wherein $R^{15}$ represents an alkyl group, and $R^{16}$ represents an aryl group which may have a substituent.)

Examples of the alkyl group represented by $R^{15}$ in formula (17) above include the above-mentioned alkyl groups.

Examples of the aryl group which may have a substituent represented by $R^{16}$ include the above-mentioned aryl groups which may have a substituent.

More specifically, examples of the alkyl aryl carbonate include methyl phenyl carbonate, ethyl phenyl carbonate, methyl tolyl carbonate, and methyl xylyl carbonate.

These carbonates can be used alone or in combination of two or more kinds.

As the carbonate, dialkyl carbonate is preferable.

In the present invention, the carbonate can be produced, for example, by a known method, or a commercially available carbonate may be used.

In order to bring the carbonate into contact with high pressure and high temperature water, the carbonate is fed into a known pressure-resistant and heat-resistant tank while high pressure and high temperature water is fed thereinto.

The high pressure and high temperature water is water which is increased in pressure to a high pressure, that is, from 3 to 30 MPa, preferably from 6 to 25 MPa, or more preferably from 6 to 20 MPa, as well as in temperature to a high temperature, that is, from 190 to 350° C., or preferably from 200 to 300° C., and is heated and pressurized by a known method.

The decomposing pressure (inner pressure) of the carbonate is in the range of 3 to 30 MPa, preferably 6 to 25 MPa, or more preferably 6 to 20 MPa. The decomposing temperature (inner temperature) of the carbonate is in the range of 190 to 350° C., or preferably 200 to 300° C.

As the high pressure and high temperature water, a hydrolytic ratio (a mass ratio of (high pressure and high temperature water/carbonate)) is controlled to, for example, 0.5 to 30, or preferably 1 to 15.

As a result of this, the carbonate is hydrolyzed with the high pressure and high temperature water to produce a corresponding alcohol as a decomposition product, more specifically, the alcohol represented by the following general formula (18), during which carbon dioxide, etc. are by-produced.

$$R^{17}\text{—OH} \tag{18}$$

(wherein $R^{17}$ represents any of $R^{11}$ or $R^{12}$ in formula (15) above, $R^{13}$ or $R^{14}$ in formula (6) above, and $R^{15}$ or $R^{16}$ in formula (17) above.)

In the method for treating carbonates, there may be used the carbonate obtained as a by-product of the carbamate formation reaction as described above, that is, the carbonate obtained as a by-product in the reaction (carbamate formation reaction) in which amine, urea and/or N-unsubstituted carbamic acid ester, and alcohol are allowed to react to thereby obtain carbamates.

Effective use of carbonate can be achieved by using the carbonate obtained as a by-product in the carbamate formation reaction.

In the carbamate formation reaction, for example, a primary amine is used as the amine.

The primary amine is an amino group-containing organic compound which has one or more primary amino groups and is represented, for example, by the following general formula (19):

$$R^{18}—(NH_2)n \qquad (19)$$

(wherein $R^{18}$ is defined as $R^{18}$ in formula (1) above.)

Illustrations and preferred embodiments of $R^{18}$ and n in formula (19) above are the same as those of $R^1$ and n in formula (1) above. Illustrations and preferred embodiments of the amine are also the same as those described above.

The N-unsubstituted carbamic acid ester is a carbamic acid ester in which a nitrogen atom of a carbamoyl group is not substituted with a functional group (i.e., the nitrogen atom is bonded to two hydrogen atoms and one carbon atom), and is represented, for example, by the following general formula (20):

$$R^{17}O—CO—NH_2 \qquad (20)$$

(wherein $R^{17}$ is defined as $R^{17}$ in formula (18) above.)

In formula (20) above, $R^{17}$ is defined as $R^{17}$ in formula (18) above, that is, $R^{17}$ represents any of $R^{11}$ or $R^{12}$ in formula (15) above, $R^{13}$ or $R^{14}$ in formula (16) above, and $R^{15}$ or $R^{16}$ in formula (17) above. More specifically, $R^{17}$ represents the above-mentioned alkyl group (alkyl group in formulae (15) and (17) above) or the above-mentioned aryl group which may have a substituent (aryl group which may have a substituent in formulae (16) and (17)).

Illustrations and preferred embodiments of the N-unsubstituted carbamic acid ester in which $R^{17}$ represents the above-mentioned alkyl group in formula (20) above are the same as those of the N-unsubstituted carbamic acid ester in which $R^2$ represents an alkyl group in formula (2) above.

Further, illustrations and preferred embodiments of the N-unsubstituted carbamic acid ester in which $R^{17}$ represents the above-mentioned aryl group which may have a substituent in formula (20) above are the same as those of the N-unsubstituted carbamic acid ester in which $R^2$ represents an aryl group in formula (2) above.

As the N-unsubstituted carbamic acid ester, N-unsubstituted carbamic acid ester in which $R^{17}$ represents an alkyl group in formula (20) above is preferable.

As the N-unsubstituted carbamic acid ester used as a raw material component for the carbamate formation reaction, although will be described in detail later, N-unsubstituted carbamic acid ester obtained by further separating from low boiling components (described later) (containing N-unsubstituted carbamic acid ester and carbonate) which have been separated after the carbamate formation reaction is preferable.

The alcohol is, for example, a primary to tertiary monohydric alcohol and is, for example, represented by the following general formula (21):

$$R^{17}—OH \qquad (21)$$

(wherein $R^{17}$ is defined as $R^{17}$ in formula (18) above.)

In formula (21) above. $R^{17}$ is defined as $R^{17}$ in formula (18) above, that is, $R^{17}$ represents any of $R^{11}$ or $R^{12}$ in formula (15) above, $R^{13}$ or $R^{14}$ in formula (16) above, and $R^{15}$ or $R^{16}$ in formula (17) above. More specifically, $R^{17}$ represents the above-mentioned alkyl group (in formulae (15) and (17) above) or the above-mentioned aryl group which may have a substituent (in formulae (16) and (17) above).

Illustrations and preferred embodiments of the alcohol in which $R^{17}$ represents the above-mentioned alkyl group in formula (21) above are the same as those of the alcohol in which $R^2$ represents an alkyl group in formula (3) above.

Further, illustrations and preferred embodiments of the alcohol in which $R^{17}$ represents the above-mentioned aryl group which may have a substituent in formula (21) above are the same as those of the alcohol in which $R^2$ represents an aryl group in formula (3) above.

As the alcohol, in formula (21) above, an alcohol in which $R^{17}$ represents an alkyl group is preferable, an alcohol in which $R^{17}$ represents an alkyl group having 1 to 8 carbon atoms is more preferable, or an alcohol in which $R^{17}$ represents an alkyl group having 2 to 6 carbon atoms is even more preferable.

As the alcohol used as the raw material component for the carbamate formation reaction, an alcohol obtained by decomposing the carbonate (formula (18) above), more specifically, an alcohol (described later) obtained by decomposing the carbonate which is obtained by further separating from low boiling components (described later) (containing N-unsubstituted carbamic acid ester and carbonate) separated after the carbamate formation reaction is preferable, although will be described in detail later.

The carbonate can be obtained as a by-product of the carbamate formation reaction by blending the amine, urea and/or N-unsubstituted carbamic acid ester, and alcohol described above and allowing the blended mixture to react preferably in a liquid phase as described above.

This reaction may be carried out, for example, by charging amine, urea and/or N-unsubstituted carbamic acid ester, alcohol, if necessary, a catalyst and a reaction solvent, in a reaction vessel under the above-mentioned conditions, and stirring or mixing the charged mixture. Then, a carbamate represented, for example, by the following general formula (22) is produced as a main product:

$$(R^{17}OCONH)n\text{-}R^{18} \qquad (22)$$

(wherein $R^{18}$ is defined as $R^{18}$ in formula (19) above; $R^{17}$ is defined as $R^{18}$ in formula (18) above; and n is defined as n in formula (19) above.)

In this reaction, ammonia is by-produced.

Further, when N-unsubstituted carbamic acid ester is blended in this reaction, an alcohol represented, for example, by the following general formula (23) is by-produced:

$$R^{17}—OH \qquad (23)$$

(wherein $R^{17}$ is defined as $R^{17}$ in formula (18) above.)

In this reaction, an N-unsubstituted carbamic acid ester represented, for example, by the following general formula (24) is by-produced:

$$R^{17}O—CO—NH_2 \qquad (24)$$

(wherein $R^{17}$ is defined as $R^{17}$ in formula (18) above.)

Further, in this reaction, a carbonate represented by the following general formula (25) is by-produced:

$$R^{17}O—CO—OR^{17} \qquad (25)$$

(wherein two $R^{17}$ may be the same or different from each other and each defined as $R^{17}$ in formula (18) above.)

In formula (25) above, two $R^{17}$ may be the same or different from each other and each defined as $R^{17}$ in formula (18) above, that is, each represents any of $R^{11}$ or $R^{12}$ in formula (15) above, $R^{13}$ or $R^{14}$ in formula (16) above, and $R^{15}$ or $R^{16}$ in formula (17) above. More specifically, two $R^{17}$ may be the same or different from each other and each represents the above-mentioned alkyl group (the alkyl group in formulae (15) and (17) above) or the above-mentioned aryl group which may have a substituent (the aryl group which may have a substituent in formulae (16) and (17) above).

When each of $R^{17}$ is an alkyl group in formula (25) above, the carbonate represented by formula (25) above is dialkyl carbonate represented by formula (15) above.

When each of $R^{17}$ is an aryl group which may have a substituent, the carbonate represented by formula (25) above is diaryl carbonate represented by formula (16) above.

Further, when one $R^{17}$ is an alkyl group and another $R^{17}$ is an aryl group which may have a substituent, the carbonate represented by formula (25) above is alkyl aryl carbonate represented by formula (17) above.

While the carbamate (formula (22) above) is separated from the obtained reaction solution by a known method, for example, excess (unreacted) urea and/or N-unsubstituted carbamic acid ester and excess (unreacted) alcohol; and alcohol (formula (23) above), N-unsubstituted carbamic acid ester (formula (24) above), and carbonate (formula (25) above) which are by-produced are separated as low boiling components (light-boiling fractions).

Then, the carbamate (formula (22) above) obtained in the carbamate formation reaction is used for the production of the isocyanate as described above.

Specifically, the carbamate (formula (22) above) obtained by the above-mentioned carbamate formation reaction is thermally decomposed, and an isocyanate represented by the following general formula (26) corresponding to the above-mentioned amine:

(wherein $R^{18}$ is defined as $R^{18}$ in formula (19) above, and n is defined as n in formula (19) above.) and an alcohol represented by the following general formula (27) which is a by-product are produced.

(wherein $R^{17}$ is defined as $R^{17}$ in formula (18) above.)

The alcohol (formula (27) above) obtained by the thermal decomposition is separated and recovered, and the recovered alcohol is then preferably used as the raw material component for the carbamate formation reaction.

As described above, when the alcohol (excess (unreacted) alcohol and by-produced alcohol (formula (23) above)), the N-unsubstituted carbamic acid ester, and the carbonate each are further roughly separated by distillation, etc. from the low boiling components (light-boiling fractions) separated from the reaction solution obtained by the carbamate formation reaction, the alcohol, the N-unsubstituted carbamic acid ester, and the carbonate each can be roughly separated and recovered.

Then, in this method, the alcohol (excess (unreacted) alcohol and by-produced alcohol) roughly separated from the low boiling components (light-boiling fractions) is used as the raw material component for the carbamate formation reaction.

Therefore, the alcohol roughly separated from the low boiling components (light-boiling fractions) can be industrially effectively used.

The N-unsubstituted carbamic acid ester roughly separated from the low boiling components (light-boiling fractions) is also used as the raw material component for the carbamate formation reaction.

Therefore, the N-unsubstituted carbamic acid ester roughly separated from the low boiling components (light-boiling fractions) can be industrially effectively used.

In this method, the carbonate roughly separated from the low boiling components (light-boiling fractions) is decomposed into alcohol by contact with high pressure and high temperature water.

At this time, when the carbonate is the carbonate (formula (25) above) obtained as a by-product by the reaction of amine, urea and/or N-unsubstituted carbamic acid ester, and alcohol, an alcohol represented by the following general formula (28) is produced as the corresponding alcohol:

(wherein $R^{17}$ is defined as $R^{17}$ in formula (18) above.)

That is, the carbonate roughly separated from the low boiling components (light-boiling fraction) is decomposed, whereby the same alcohol as the one represented by formula (21) above as the raw material component for the carbamate formation reaction is produced.

In the rough separation of the low boiling components (light-boiling fractions), N-unsubstituted carbamic acid ester may be contained in the carbonate. Even in such case, the carbonate and the N-unsubstituted carbamic acid ester can be decomposed into alcohol at once by contact with high pressure and high temperature water.

In this method, the alcohol (formula (28) above) obtained by decomposing the carbonate is preferably used as the raw material component for the carbamate formation reaction.

Therefore, the alcohol obtained by decomposing the carbonate roughly separated from the low boiling components is used as a raw material component for the carbamate formation reaction, whereby the carbonate by-produced in the carbamate formation reaction can be industrially effectively used.

As a result of this, according to the method for treating carbonates of the present invention, since the carbonate can be decomposed into alcohol, the carbonate can be industrially effectively used.

Figure 3:
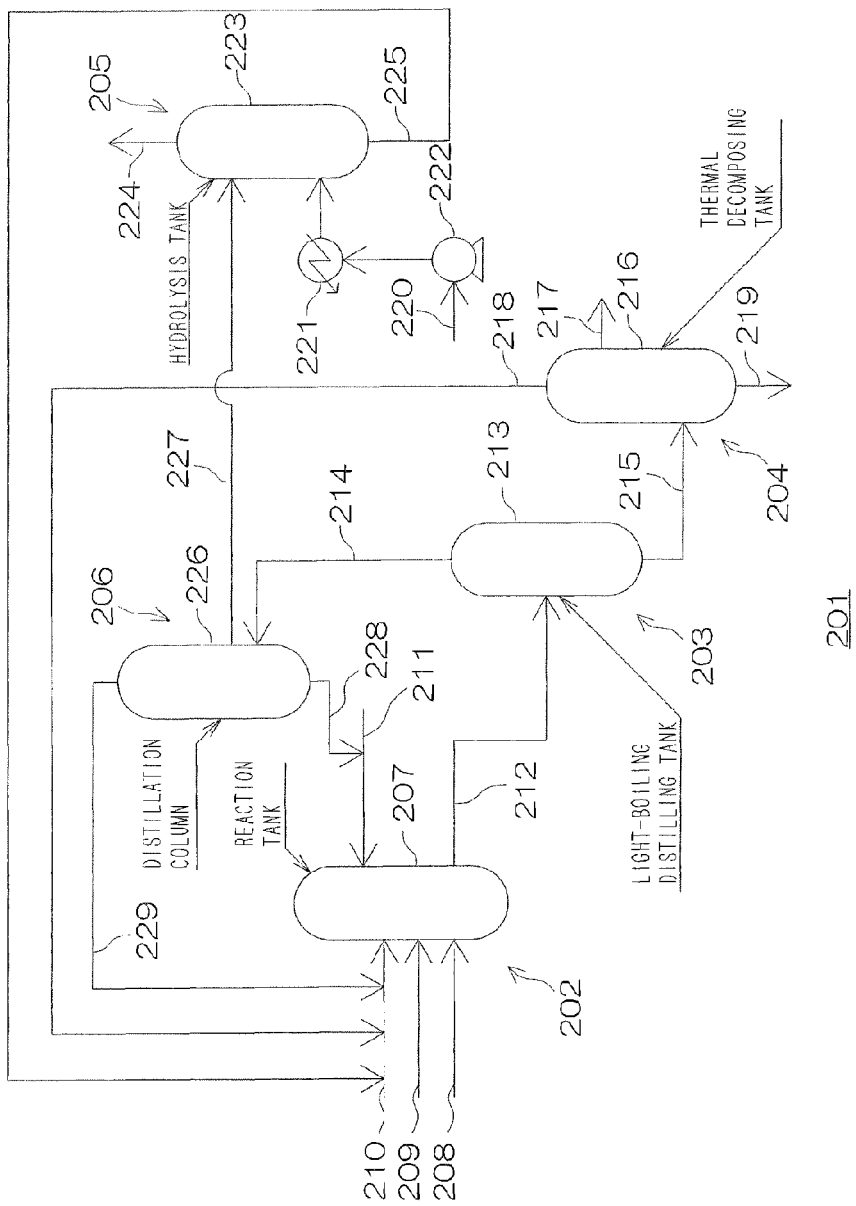
FIG. 3 is a schematic configuration diagram showing one embodiment of a plant employing a method for treating carbonates according to the present invention.

FIG. 3 is a schematic configuration diagram showing one embodiment of a plant employing a method for treating carbonates according to the present invention.

One embodiment of the plant where the above-mentioned method for treating carbonates is industrially carried out is described below with reference to FIG. 3.

In FIG. 3, the plant 201 is an isocyanate production system which employs the above-mentioned method for treating carbonates, and includes a reaction system 202, a light-boiling distillation system 203, a thermal decomposing system 204, a distillation system 206, and a hydrolysis system 205.

The reaction system 202 is equipped in the plant 201, for the purpose of producing carbamates by reaction of amine, urea and/or N-unsubstituted carbamic acid ester, and alcohol.

The reaction system 202 includes a reaction tank 207, and an amine feed pipe 208, a urea feed pipe 209, a carbamic acid ester feed pipe 211, and an alcohol feed pipe 210 which are connected to the reaction tank 207.

The reaction tank 207 is a carbamate formation reaction tank for carbamates to be produced by carbamate formation reaction of amine, urea and/or N-unsubstituted carbamic acid ester, and alcohol. It has a heat-resistant and pressure-resistant vessel whose temperature and pressure can be controlled.

Though not shown, for example, a catalyst feed pipe which feeds a catalyst to the reaction tank 207, an inert gas feed pipe for substituting air for inert gas (e.g., nitrogen gas) in the reaction tank 207, a stirrer for stirring in the reaction tank 207, and an ammonia drain pipe which distills by-produced ammonia out of the system may be provided as required in the reaction tank 207.

The amine feed pipe 208 is an amine feed line for feeding amine to the reaction tank 207, and the downstream end thereof is connected to the reaction tank 207. Though not shown, the upstream end thereof is connected to an amine introducing line for introducing amine.

The urea feed pipe 209 is a urea feed line for feeding urea to the reaction tank 207, and the downstream end thereof is connected to the reaction tank 207. Though not shown, the upstream end thereof is connected to a urea introducing line for introducing urea.

The carbamic acid ester feed pipe 211 is an N-unsubstituted carbamic acid ester feed line for feeding N-unsubstituted carbamic acid ester to the reaction tank 207, and the downstream end thereof is connected to the reaction tank 207. Though not shown, the upstream end thereof is connected to an N-unsubstituted carbamic acid ester introducing line for introducing N-unsubstituted carbamic acid ester.

The downstream end of a carbamic acid ester reflux pipe 228 (described later) is connected to the carbamic acid ester feed pipe 211 at a location in its flow direction.

The alcohol feed pipe 210 is an alcohol feed line for feeding alcohol to the reaction tank 207, and the downstream end thereof is connected to the reaction tank 207. Though not shown, the upstream end thereof is connected to an alcohol introducing line for introducing alcohol.

The downstream end of a first alcohol reflux pipe 218 (described later), the downstream end of a second alcohol reflux pipe 225, and the downstream end of a third alcohol reflux pipe 229 (described later) are connected to the alcohol feed pipe 210 at locations in their flow direction.

The light-boiling distillation system 203 is equipped in the plant 201, for the purpose of separating low boiling components (light-boiling fractions) such as excess (unreacted) alcohol, urea and/or N-unsubstituted carbamic acid ester; and alcohol, N-unsubstituted carbamic acid ester, and carbonate which are by-products, from the reaction solution obtained in the reaction tank 207.

The light-boiling distillation system 203 includes a light-boiling distilling tank 213 and a first reaction-solution transporting pipe 212 connected to the light-boiling distilling tank 213.

The light-boiling distilling tank 213 is a distilling tank for distilling off the above-mentioned low boiling components from the reaction solution obtained in the reaction system 202. It has a heat-resistant and pressure-resistant vessel whose temperature and pressure can be controlled.

The first reaction-solution transporting pipe 212 is a first reaction-solution transporting line for transporting the reaction solution produced in the reaction system 202 to the light-boiling distilling tank 213, of which the downstream end is connected to the light-boiling distilling tank 213 and the upstream end is connected to the reaction tank 207 in the reaction system 202.

The thermal decomposing system 204 is equipped in the plant 201, for the purpose of decomposing the reaction solution into isocyanate and alcohol.

The thermal decomposing system 204 include a thermal decomposing tank 216, and a second reaction-solution transporting pipe 215, an isocyanate drain pipe 217, and an isocyanate residue drain pipe 219.

The thermal decomposing tank 216 is a decomposing tank for the reaction solution obtained in the reaction system 202 to be decomposed into isocyanate and alcohol by heating. It has a heat-resistant and pressure-resistant vessel whose temperature and pressure can be controlled.

Though not shown, for example, a solvent feed pipe which feeds a solvent to the thermal decomposing tank 216 may be provided as required in the thermal decomposing tank 216.

The second reaction-solution transporting pipe 215 is a second reaction-solution transporting line for transporting the reaction solution in which the light-boiling fractions have been distilled off in the light-boiling distillation system 203, to the thermal decomposing tank 216, of which the downstream end is connected to the thermal decomposing tank 216 and the upstream end is connected to the light-boiling distilling tank 213 in the light-boiling distillation system 203.

The isocyanate drain pipe 217 is an isocyanate drain line for draining the isocyanate obtained by the thermal decomposition of the reaction solution out of the plant 201, and the upstream end thereof is connected to the thermal decomposing tank 216. Though not shown, the downstream end thereof is connected to an isocyanate purifying line for purifying the isocyanate.

The isocyanate residue drain pipe 219 is a residue drain line for draining isocyanate residues (residues obtained by the thermal decomposition of the reaction solution) produced in the thermal decomposing system 204, and the upstream end thereof is connected to the thermal decomposing tank 216. Though not shown, the downstream end thereof is connected to an isocyanate residue storage tank.

The distillation system 206 is equipped in the plant 201, for the purpose of roughly separating alcohol, N-unsubstituted carbamic acid ester, and carbonate from the low boiling components (light-boiling fractions) obtained in the light-boiling distilling tank 213.

The distillation system 206 includes a distillation column 226 and a light-boiling fraction transporting pipe 214 connected to the distillation column 226.

The distillation column 226 is a separation column for roughly separating the N-unsubstituted carbamic acid ester as well as the carbonate, and further roughly separating the alcohol from the low boiling components (light-boiling fractions) obtained in the light-boiling distillation system 203. It has a known distillation column.

The light-boiling fraction transporting pipe 214 is a light-boiling fraction transporting line for transporting the low boiling components (light-boiling fractions) obtained in the light-boiling distillation system 203 to the distillation system 206, of which the downstream end is connected to the distillation column 226 and the upstream end is connected to the light-boiling distilling tank 213 in the light-boiling distillation system 203.

The hydrolysis system 205 is equipped in the plant 201, for the purpose of decomposing the carbonate roughly separated by the distillation system 206 into alcohol using high pressure and high temperature water.

The hydrolysis system 205 includes a hydrolysis tank 223, and a carbonate transporting pipe 227 and a water feed pipe 220 which are connected to the hydrolysis tank 223.

The hydrolysis tank 223 is a hydrolysis tank for hydrolyzing the carbonate by contact of the carbonate with high pressure and high temperature water to give alcohol. It has a heat-resistant and pressure-resistant vessel whose temperature and pressure can be controlled.

A drain pipe 224 which drains the carbon dioxide by-produced by the hydrolysis of the carbonate and the water or the like used for the hydrolysis from the plant 201 is provided in the hydrolysis tank 223.

Though not shown, for example, a stirrer for stirring in the hydrolysis tank 223 may be provided in the hydrolysis tank 223 as required.

The carbonate transporting pipe 227 is a carbonate transporting line for transporting the carbonate recovered in the distillation system 206 to the hydrolysis system 205, of which the upstream end is connected to the distillation column 226 and the downstream end is connected to the hydrolysis tank 223 in the hydrolysis system 205.

A carbonate pressure-feed pump (not shown) for pressure-transporting the carbonate toward the hydrolysis tank 223 is interposed as required in the carbonate transporting pipe 227. Further, a carbonate heater (not shown) for heating the carbonate is interposed as required on the downstream side of the carbonate pressure-feed pump (not shown).

The water feed pipe 220 is a water feed line for feeding high pressure and high temperature water to the hydrolysis tank 223. It has a heat-resistant and pressure-resistant pipe of which the downstream end is connected to the hydrolysis tank 223 and the upstream end is connected to a water feed line for feeding water (recovered process water, ion-exchange water, etc.) not shown.

A water pressure-feed pump 222 for pressure-transporting the high pressure and high temperature water toward the hydrolysis tank 223 is interposed in the water feed pipe 220. A water heater 221 for heating water is further interposed in the water feed pipe 220 at a location on the downstream side of the water pressure-feed pump 222.

The plant 201 further includes a first alcohol reflux pipe 218, a second alcohol reflux pipe 225, a third alcohol reflux pipe 229, and a carbamic acid ester reflux pipe 228.

The first alcohol reflux pipe 218 is a first alcohol reflux line for refluxing the alcohol, which has been obtained by thermally decomposing the reaction solution in the thermal decomposing system 204, to the alcohol feed pipe 210 in the reaction system 202, of which the upstream end is connected to the thermal decomposing tank 216 and the downstream end is connected to a location in the flow direction of the alcohol feed pipe 210.

The second alcohol reflux pipe 225 is a second alcohol reflux line for refluxing the alcohol, which has been obtained by hydrolyzing the carbonate in the hydrolysis system 205, to the alcohol feed pipe 210 in the reaction system 202, of which the upstream end is connected to the hydrolysis tank 223 and the downstream end is connected to a location in the flow direction of the alcohol feed pipe 210.

The third alcohol reflux pipe 229 is a third alcohol reflux line for refluxing the alcohol, which has been obtained by distilling the low boiling components (light-boiling fractions) in the distillation system 206, to the alcohol feed pipe 210 in the reaction system 202, of which the upstream end is connected to the distillation column 226 and the downstream end is connected to a location in the flow direction of the alcohol feed pipe 210.

The carbamic acid ester reflux pipe 228 is a carbamic acid ester reflux line for refluxing the N-unsubstituted carbamic acid ester, which has been obtained by distilling the low boiling components (light-boiling fractions) in the distillation system 206, to the carbamic acid ester feed pipe 211 in the reaction system 202, of which the upstream end is connected to the distillation column 226 and the downstream end is connected to a location in the flow direction of the carbamic acid ester feed pipe 211.

Next, the following method will be described below: carbamates and isocyanates are produced in the plant 201 while carbonate is roughly separated from the low boiling components obtained in the production of the carbamate and then decomposed, so that the resulting alcohol is used again as the raw material component for the carbamate formation reaction.

In this method, first, carbamate is produced in the reaction system 202.

In the production of the carbamate, the reaction system 202 is continuously operated to pressure-transport amine, urea and/or N-unsubstituted carbamic acid ester, and alcohol, which are a raw material for the carbamate, from the amine feed pipe 208, the urea feed pipe 209 and/or the carbamic acid ester feed pipe 211, and the alcohol feed pipe 210, respectively, at the above-mentioned proportion, thereby continuously feeding them to the reaction tank 207. In addition to these raw material components, a catalyst is fed from a catalyst feed pipe (not shown) as required.

In this method, the amine, urea and/or N-unsubstituted carbamic acid ester, and alcohol are subjected to carbamate formation reaction in the reaction tank 207, so that a reaction solution containing carbamate, and alcohol, N-unsubstituted carbamic acid ester and carbonate which are by-produced is obtained.

The reaction solution thus obtained is fed to the first reaction-solution transporting pipe 212 and is then pressure-transported to the light-boiling distillation system 203.

Next, in this method, low boiling components (light-boiling fractions) such as excess (unreacted) alcohol, urea and/or N-unsubstituted carbamic acid ester; and alcohol, N-unsubstituted carbamic acid ester, and carbonate which are by-products, are separated from the reaction solution in the light-boiling distillation system 203 (light-boiling distilling tank 213).

The light-boiling fractions separated in the light-boiling distilling tank 213 are introduced into the light-boiling fraction transporting pipe 214 and then fed to the distillation system 206.

In this method, the low boiling components (light-boiling fractions) fed to the distillation system 206 are distilled in the distillation column 226, to thereby roughly separate the N-unsubstituted carbamic acid ester, the carbonate, and the alcohol (containing excess (unreacted) alcohol and by-produced alcohol).

The N-unsubstituted carbamic acid ester thus roughly separated is introduced into the carbamic acid ester reflux pipe 228, and then refluxed to the carbamic acid ester feed pipe 211. As a result, the N-unsubstituted carbamic acid ester is fed to the reaction tank 207.

Also, the alcohol thus roughly separated is introduced into the third alcohol reflux pipe 229 and then refluxed to the alcohol feed pipe 210. As a result, the alcohol is fed to the reaction tank 207.

The carbonate (which may contain the N-unsubstituted carbamic acid ester in some cases) is fed to the carbonate transporting pipe 227 and then pressure-transported to the hydrolysis system 205.

Next, in this method, the carbonate is hydrolyzed in the hydrolysis system 205.

In the hydrolysis of the carbonate, while the hydrolysis system 205 is continuously operated, the carbonate fed from the distillation system 206 (distillation column 226) via the carbonate transporting pipe 227 is decomposed on the above conditions in the hydrolysis tank 223.

Specifically, in this method, the carbonate is fed to the hydrolysis tank 223 via the carbonate transporting pipe 227 in the state of being increased in pressure to a feeding pressure of, for example, 3 to 30 MPa and being heated to a feeding temperature of, for example, 190 to 350° C.

On the other hand, the water flowing into the water feed pipe 220 from the water feed line is pressure-transported through the water feed pipe 220 by the water pressure-feed pump 222, flowing toward the hydrolysis tank 223, during which the water is heated by the water heater 221. As a result, the water is increased in pressure to 3 to 30 MPa as well as in temperature to 190 to 350° C., thereby to become a high pressure and high temperature water. Then, the high pressure and high temperature water is flown into the hydrolysis tank 223.

The hydrolysis tank 223 is controlled to an inner temperature (decomposing temperature) of, for example, 190 to 350° C. and an inner pressure (decomposing pressure) of, for example, 3 to 30 MPa. Further, a hydrolytic ratio (a mass ratio of (high pressure and high temperature water/carbonate)) is controlled to, for example, 0.5 to 30 under control of the carbonate pressure-feed pump (not shown) and the water pressure-feed pump 222.

As a result of this, in the hydrolysis tank 223, the carbonate (which may contain the N-unsubstituted carbamic acid ester in some cases) is continuously hydrolyzed with the high pressure and high temperature water to produce corresponding alcohol as a decomposition product, and the by-produced carbon dioxide and the water used for the hydrolysis are drained from the plant 201 via the drain pipe 224.

Further, the produced alcohol is continuously separated, introduced into the second alcohol reflux pipe 225, and then refluxed to the alcohol feed pipe 210. As a result, the alcohol is fed to the reaction tank 207.

On the other hand, in the light-boiling distillation system 203, the reaction solution obtained as a residue after the light-boiling fractions are separated from the reaction solution is fed to the second reaction-solution transporting pipe 215 and then pressure-transported to the thermal decomposing system 204.

Next, in this method, the reaction solution is thermally decomposed in the thermal decomposing system 204.

In the thermal decomposition of the reaction solution, while the thermal decomposing system 204 is continuously operated, the reaction solution fed via the second reaction-solution transporting pipe 215 is heated and thermally decomposed on the above conditions in the thermal decomposing tank 216.

Thus, a decomposition solution including isocyanate and alcohol is obtained, and isocyanate residues are also obtained as well as the isocyanate and the alcohol.

The isocyanate obtained in the thermal decomposing tank 216 is drained via the isocyanate drain pipe 217 and then transported to the isocyanate purifying line which is not shown.

On the other hand, the alcohol obtained in the thermal decomposing tank 216 is introduced into the first alcohol reflux pipe 218 after separated from the decomposition solution, and then refluxed to the alcohol feed pipe 210. As a result, the alcohol is fed to the reaction tank 207.

The isocyanate residues obtained in the thermal decomposing tank 216 is transported to an isocyanate residue storage tank (not shown) via the isocyanate residue drain pipe 219, and then temporarily stored in the isocyanate residue storage tank (not shown). Thereafter, the stored isocyanate residues are incinerated, disposed of, or recycled, for example.

With the plant 201, isocyanate is continuously produced while the alcohol, the N-unsubstituted carbamic acid ester, and the carbonate which are obtained as by-products are roughly separated, and the alcohol and the N-unsubstituted carbamic acid ester, and further the alcohol obtained by decomposing the carbonate are refluxed, so that they can be efficiently used.

In the foregoing, the method for treating carbonates has been discussed. However, the plant 201 can include a pre-treatment system for carrying out pre-treatment steps including a dehydration step, and a post-treatment system for carrying out post-treatment steps including intermediate steps, a distillation step, a filtration step, a purification step, and a recovery step, in appropriate positions as required.

EXAMPLES

While in the following, the present invention will be described in further detail with reference to Examples, the present invention is not limited to any of them.

1. Treating Method for Bringing Isocyanate Residues into Contact with High Pressure and High Temperature Water in the Presence of Solvent <Definition of Recovering Rate (mol %) of 2,4-Tolylenediamine>

The recovering rate (mol %) of 2,4-diaminotoluene (hereinafter referred to as 2,4-TDA) indicates the amount (mol) of 2,4-TDA actually recovered with respect to the theoretical amount (mol) of 2,4-TDA obtained based on the assumption that all the acetone-insoluble filter residues introduced into a reactor are determined as 2,4-bis(butoxycarbonylamino)toluene (hereinafter referred to as 2,4-TDC), and further all the amount of 2,4-TDC is recovered as 2,4-TDA.

<Preparation of Isocyanate Residues (Compound Containing Urea and/or Carbamate, and Derivative(s) Thereof)>

Preparation Example 1

(1) Carbamate Formation Reaction

A 1-liter SUS autoclave equipped with a pressure control valve, a reflux condenser, a gas-liquid separator, and a stirrer was charged with a mixture of 2,4-TDA (76.5 g:0.626 mol), urea (113 g:1.87 mol), and 1-butanol (255 g:3.44 mol), and further charged with a mixture of zinc p-toluenesulfonate (0.64 g:1.57 mmol) as a catalyst and 1-butanol (23.4 g:316 mmol). While a nitrogen gas was allowed to flow at 1 liter per minute and stirred at 500 rpm, the charged mixture was allowed to react for 4 hours during which the internal pressure was controlled with the pressure control valve so that the reaction temperature was maintained at 215° C.

When a portion of the reaction solution was sampled and quantified, it was confirmed that 2,4-bis(butoxycarbonylamino)toluene was produced at a yield of 86.4% by mol based on 2,4-diaminotoluene. It was also confirmed that mono(butoxycarbonylamino)aminotoluene was produced at a yield of 3.2% by mol.

(2) Vacuum Distillation of Light-Boiling Fractions

A 500-ml glass four-neck flask equipped with a stirrer and a condenser tube was charged with 375 g of the reaction solution obtained by the above-mentioned carbamate formation reaction, and while the charged mixture was stirred at 230 rpm, the pressure in the vessel was reduced to 2 kPa with a vacuum pump. The temperature in the vessel was increased to 100° C. with circulation water of 25° C. flowing through the condenser tube, so that the reaction solution was condensed. Subsequently, the temperature of the circulation water was set to 80° C., and the temperature in the vessel was increased to 180° C., so that the reaction solution was condensed, to finally obtain a brown concentrate amounting to 193 g.

(3) Thermal Decomposition of Carbamate, and Separation and Recovery of Isocyanate Residues A 500-ml glass four-neck flask equipped with a stirrer and a rectifying column having a reflux pipe at its upper portion was charged with 72 g of the concentrate obtained by the vacuum distillation of the light-boiling fractions as described above and 140 g of barrel process oil B-05 (manufactured by Matsumura Oil Co., Ltd.) as a solvent. While the temperature of the circulation water in the reflux pipe was set to 90° C. and the charged mixture was stirred at 230 rpm, the pressure in the system was reduced to 100 hPa with a vacuum pump.

Next, the temperature was increased by setting the temperature of the thermometer in the reactor to 250° C., so that the temperature at the top of the column increased. At this time, it was confirmed that tolylene diisocyanate (hereinafter referred to as TDI) began to condense in the reflux pipe. Then, the reflux ratio was set at 5 (=reflux for 10 seconds/distillation for 2 seconds) to distill off the reflux liquid.

After 1 hour, it was confirmed that the distillation was completed and that a TOP temperature in the rectifying column decreased. Then, the heating was stopped and the reaction solution was filtered with 5A filter paper, to thereby be separated into a filtrate and a filter residue.

Thereafter, the filter residue was recovered after washed using acetone and then dried together with solids adhering to the wall of the reaction vessel, so that a yellowish brown acetone-insoluble filter residue amounting to 7.0 g was obtained. <Hydrolysis of Isocyanate Residues (Carbamate Thermal Decomposition Residues)>(Example 1) A 36-mL SUS autoclave equipped with a thermocouple and a pressure regulating valve was charged with 3.0 g of the acetone-insoluble filter residue obtained in Preparation Example 1 and 5.8 g of barrel process oil B-05, and the system was further filled with ion exchange water. The reactor was placed in an electric furnace, and the charged mixture was allowed to react for 20 minutes while the internal pressure was adjusted with the pressure regulating valve so that the reaction temperature and the internal pressure were maintained at 280° C. and 20 MPa, respectively. At this time, the hydrolytic ratio (a mass ratio of (ion exchange water (high pressure and high temperature water)/acetone-insoluble filter residues (isocyanate residues)) was set at 9.

As a result, it was confirmed that after the reactor was cooled to room temperature, no solid remained in the recovered reaction solution and all the filter residues were decomposed. When a portion of the reaction solution was sampled and quantified with a liquid chromatograph (a UV detector (254 nm) and an RI detector), the recovery rate of 2,4-TDA was found to be 83.5% by mol.

Example 2

The same procedures as in Example 1 were carried out except that the reaction temperature was set to 190° C., to perform the decomposition reaction of the carbamate thermal decomposition residues.

After the reactor was cooled to room temperature, no solid remained in the recovered reaction solution. The result of HPLC analysis of the reaction solution showed that the recovery rate of 2,4-TDA was 33.9% by mol.

Comparative Example 1

A 36-mL SUS autoclave equipped with a thermocouple and a pressure regulating valve was charged with 3.0 g of the acetone-insoluble filter residue obtained in Preparation Example 1 but not charged with barrel process oil B-05. The system was filled with ion exchange water. As a result of this, the acetone-insoluble filter residue repelled water and floated to the liquid surface without getting wet. Then, the reactor was placed in an electric furnace with the filter residue remaining in such state, and the temperature in the reactor was increased to 260° C. while the pressure was adjusted with the pressure regulating valve so that the pressure was maintained at 20 MPa. In the meanwhile, the reaction was interrupted because a blockage in the line was observed. <Confirmation of Hydrolysis Resistance of Barrel Process Oil B-05>

Reference Example 1

The following operation confirmed that the solvent used for the thermal decomposition in Preparation Example 1 did not react under the hydrolysis conditions of the isocyanate residues obtained by thermal decomposition.

The same reactor as used in Example 1 was charged with 7.3 g of barrel process oil B-05 and the system was further filled with ion exchange water. The reactor was placed in an electric furnace and heated to 320° C. Thereafter, the temperature was maintained for 20 minutes and the heating was then stopped. The pressure during the reaction was adjusted with the pressure regulating valve so that the pressure was maintained at 20 MPa. After the reactor was cooled to room temperature, the recovered reaction solution was measured with a gas chromatograph. As a result of this, no significant difference was confirmed as compared with a preparation, and no peak considered as a decomposed product was detected.

2. Treating Method for Blending Carbonate with Isocyanate Residues and Bringing them into Contact with High Pressure and High Temperature Water
<Conversion>

Conversion (%)=(moles of carbonate consumed)/
((moles of carbonate fed to the reactor)−(moles of carbonate drained from the pressure regulating valve during the reaction))×100

<Recovering Rate of TDA>

The recovery (mol %) of a mixture (hereinafter referred to as TDA) of 2,4-diaminotoluene and 2,6-diaminotoluene (a mass ratio of 80/20) indicates the amount (mol) of TDA actually obtained with respect to the theoretical amount (mol) of TDA obtained based on the assumption that all the acetone-insoluble filter residues introduced into the reactor are determined as bis(butoxycarbonylamino)toluene (hereinafter referred to as TDC:), and further all the amount of TDC is recovered in the form of TDA.

Preparation Example 2

(1) Carbamate Formation Reaction

A 1-liter SUS autoclave equipped with a pressure control valve, a reflux condenser, a gas-liquid separator, and a stirrer was charged with TDA (80.6 g:0.661 mol), urea (113 g:1.88 mol), and 1-butanol (255 g:3.44 mol), and further charged with a mixture of zinc p-toluenesulfonate (0.64 g:1.57 mmol) as a catalyst and 1-butanol (23.4 g:316 mmol). While a nitrogen gas was allowed to flow at 1 liter per minute and stirred at 500 rpm, the charged mixture was allowed to react for 4 hours during which the internal pressure was adjusted with the pressure control valve so that the reaction temperature was maintained at 215° C. Therefore, a reaction solution amounting to 410 g was obtained.

When a portion of the reaction solution was sampled and quantified, it was confirmed that 2,4-bis(butoxycarbonylamino)toluene (hereinafter referred to as 2,4-TDC) amounts to 38.9% by mass, 2,6-bis(butoxycarbonylamino)toluene (hereinafter referred to as 2,6-TDC) amounts to 9.48% by mass, 1-butanol amounts to 33.2% by mass, butyl carbamate amounts to 13.2% by mass, and dibutyl carbonate amounts to 2.83% by mass.

(2) Vacuum Distillation of Light-Boiling Fractions

A 500-ml glass four-neck flask equipped with a stirrer and a condenser tube was charged with 387.77 g of the reaction solution obtained by the above-mentioned carbamate formation reaction, and while the charged mixture was stirred at 200 rpm, the pressure in the vessel was reduced to 2 kPa with a vacuum pump. The temperature in the vessel was increased to 100° C. with circulation water of 25° C. flowing through the condenser tube, so that the carbamate formation reaction solution was condensed, to finally distill off 125.44 g of light-boiling fractions.

The light-boiling fractions thus distilled off were analyzed with a high-performance liquid chromatograph (HPLC) and a gas chromatograph (GC), and the result confirmed that the light-boiling fractions primarily contained butanol. Subsequently, the temperature of the circulation water was set to 70° C., the temperature in the vessel was increased to 180° C., so that the carbamate formation reaction solution was condensed, to finally obtain a brown concentrate amounting to 195.89 g and light-boiling fractions amounting to 63.19 g.

The light-boiling fractions were analyzed with HPLC and GC, and the result confirmed that the light-boiling fractions primarily contained butyl carbamate and dibutyl carbonate.

(3) Thermal Decomposition of Carbamate, and Separation and Recovery of Isocyanate Residues A 500-ml glass four-neck flask equipped with a stirrer and a rectifying column having a reflux pipe at its upper portion was charged with 196 g of the concentrate obtained by the vacuum distillation of the light-boiling fractions as described above and 196 g of barrel process oil 13-05 (manufactured by Matsumura Oil Co. Ltd.) as a solvent. While the temperature of the circulation water in the reflux pipe was set to 90° C. and the charged mixture was stirred at 230 rpm, the pressure in the system was reduced to 100 hPa with a vacuum pump.

Next, the temperature was increased by setting the temperature of the thermometer in the reactor to 250° C., so that the temperature at the top of the column increased. At this time, it was confirmed that tolylene diisocyanate (hereinafter referred to as TDI) began to condense in the reflux pipe. Then, the reflux ratio was set at 5 (=reflux for 10 seconds/distillation for 2 seconds) to distill off the reflux liquid.

It was confirmed that the distillation was completed 240 minutes after the temperature increase. Then, the heating was stopped and the reaction solution was filtered with 5A filter paper, to thereby be separated into a filtrate and a filter residue.

Thereafter, the filter residue was recovered after washed using acetone and then dried together with solids adhering to the wall of the reaction vessel, so that a brown acetone-insoluble filter residue amounting to 6.33 g was obtained.

(4) Separation of Butyl Carbamate and Dibutyl Carbonate

To a distiller filled with a packing corresponding to 20 theoretical plates, 63.19 g of the mixture of butyl carbamate and dibutyl carbonate (butyl carbamate: 90.9% by mass, dibutyl carbonate: 9.1% by mass) obtained by the vacuum distillation of the light-boiling fractions as described above was fed and then distilled under the conditions of a pressure of 20 mmHg, to thereby obtain 6.36 g of dibutyl carbonate containing about 10% by mass of butyl carbamate.

Example 3

A 36-mL SUS autoclave equipped with a thermocouple and a pressure regulating valve was charged with 1.00 g of the acetone-insoluble filter residue obtained in Preparation Example 2 and 2.12 g of the dibutyl carbonate obtained in Preparation Example 2, and the system was further filled with ion exchange water. The reactor was placed in an electric furnace, and the charged mixture was allowed to react for 20 minutes while the internal pressure was adjusted with the pressure regulating valve so that the reaction temperature and the internal pressure were maintained at 280° C. and 20 MPa, respectively. At this time, the hydrolytic ratio (a mass ratio of (ion exchange water/(dibutyl carbonate+acetone-insoluble filter residues)) was set at 11.

After the reactor was cooled to room temperature, a portion of the reaction solution was sampled and quantified with HPLC. As a result, it was confirmed that the recovery rate of TDA was 73.5% by mol, the conversion of dibutyl carbonate was 100%, and the recovery rate of butanol was 75.5% by mol.

Example 4

A 36-mL SUS autoclave equipped with a thermocouple and a pressure regulating valve was charged with 1.00 g of the acetone-insoluble filter residue obtained in Preparation Example 2 and 2.12 g of dibutyl carbonate (DIALCARB M-2 manufactured by Mitsui Fine Chemicals, Inc.), and the charged mixture was subjected to decomposition reaction by the same procedures as in Example 3.

After the reactor was cooled to room temperature, a portion of the reaction solution was sampled and quantified with HPLC. As a result, it was confirmed that the recovery rate of TDA was 76.1% by mol, the conversion of dibutyl carbonate was 100%, and the recovery rate of butanol was 79.0% by mol.

3. Carbonate Treating Method

<Conversion>

Conversion (%)=(moles of carbonate consumed)/
((moles of carbonate fed to the reactor)−(moles of carbonate drained from the pressure regulating valve during the reaction))×100

<Selectivity>

Selectivity (mol %)=(moles of alcohol produced/2)/
(moles of carbonate consumed)×100

Preparation Example 3

(1) Carbamate Formation Reaction

A 1-liter SUS autoclave equipped with a pressure control valve, a reflux condenser, a gas-liquid separator, and a stirrer was charged with a mixture (hereinafter referred to as TDA) (80.6 g:0.661 mol) of 2,4-diaminotoluene and 2,6-diaminotoluene (a mass ratio of 80/20), urea (113 g:1.88 mol), and 1-butanol (255 g:3.44 mol), and further charged with a mixture of zinc p-toluenesulfonate (0.64 g:1.57 mmol) as a catalyst and 1-butanol (23.4 g:316 mmol). While a nitrogen gas was allowed to flow at 1 liter per minute and stirred at 500 rpm, the charged mixture was allowed to react for 4 hours during which the internal pressure was adjusted with the pressure control valve so that the reaction temperature was maintained at 215° C. Therefore, a reaction solution amounting to 410 g was obtained.

When a portion of the reaction solution was sampled and quantified, it was confirmed that 2,4-bis(butoxycarbonylamino)toluene amounts to 38.9% by mass, 2,6-bis(butoxycarbonylamino)toluene amounts to 9.48% by mass, 1-butanol amounts to 33.2% by mass, butyl carbamate amounts to 13.2% by mass, and dibutyl carbonate amounts to 2.83% by mass.

(2) Vacuum Distillation of Light-Boiling Fractions

A 500-ml glass four-neck flask equipped with a stirrer and a condenser tube was charged with 387.77 g of the reaction solution obtained by the above-mentioned carbamate formation reaction, and while the charged mixture was stirred at 200 rpm, the pressure in the vessel was reduced to 2 kPa with a vacuum pump. The temperature in the vessel was increased to 100° C. with circulation water of 25° C. flowing through the condenser tube, so that the reaction solution was condensed, to finally distill off 125.44 g of light-boiling fractions.

The light-boiling fractions thus distilled off were analyzed with a high-performance liquid chromatograph (HPLC) and a gas chromatograph (GC), and the result confirmed that the light-boiling fractions primarily contained butanol. Subsequently, the temperature of the circulation water was set to 70° C., the temperature in the vessel was increased to 180° C., so that the reaction solution was condensed, to finally obtain a brown concentrate amounting to 195.89 g and light-boiling fractions amounting to 63.19 g.

The light-boiling fractions were analyzed with HPLC and GC, and the result confirmed that the light-boiling fractions primarily contained butyl carbamate and dibutyl carbonate.

(3) Separation of Butyl Carbamate and Dibutyl Carbonate

To a distiller filled with a packing corresponding to 20 theoretical plates, 63.19 g of the mixture of butyl carbamate and dibutyl carbonate (butyl carbamate: 90.9% by mass, dibutyl carbonate: 9.1% by mass) obtained by the vacuum distillation of the light-boiling fractions as described above was fed and then distilled under the conditions of a pressure of 20 mmHg, to thereby obtain 6.36 g of dibutyl carbonate containing about 10% by mass of butyl carbamate.

Example 5

A 36-mL SUS autoclave equipped with a thermocouple and a pressure regulating valve was charged with 3.17 g of the dibutyl carbonate containing about 10% of butyl carbamate obtained in Preparation Example 3, and the system was further filled with ion exchange water.

The reactor was placed in an electric furnace, and the charged mixture was allowed to react for 20 minutes while the internal pressure was adjusted with the pressure regulating valve so that the reaction temperature and the internal pressure were maintained at 280° C. and 20 MPa, respectively. At this time, the hydrolytic ratio (a mass ratio of (ion exchange water/dibutyl carbonate)) was set at 11.

After the reactor was cooled to room temperature, a portion of the reaction solution was sampled and quantified with HPLC. As a result of this, it was confirmed that the conversion of dibutyl carbonate was 100% and the selectivity of n-butanol was 95.0% by mol.

Example 6

A 36-mL SUS autoclave equipped with a thermocouple and a pressure regulating valve was charged with 3.04 g of dibutyl carbonate (DIALCARB M-2 manufactured by Mitsui Fine Chemicals, Inc.), and the charged one was subjected to decomposition reaction by the same procedures as in Example 5.

After the reactor was cooled to room temperature, a portion of the reaction solution was sampled and quantified with HPLC. As a result of this, it was confirmed that the conversion of dibutyl carbonate was 100% and the selectivity of n-butanol was 92.9% by mol.

Example 7

The dibutyl carbonate was subjected to decomposition reaction by the same procedures as in Example 6 except that the reaction temperature was set to 200° C.

After the reactor was cooled to room temperature, the recovered reaction solution was analyzed with HPLC. As a result of this, it was confirmed that the conversion of dibutyl carbonate was 3.3% and the selectivity of n-butanol was 99% by mol.

Example 8

The same procedures as in Example 6 were carried out to charge 2.58 g of diphenyl carbonate, and the charged one was then subjected to decomposition reaction.

After the reactor was cooled to room temperature, a portion of the recovered reaction solution was sampled and quantified with GC. As a result of this, it was confirmed that the conversion of diphenyl carbonate was 100% and the selectivity of phenol was 99% by mol.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The method for treating isocyanate residues according to the present invention can be used for treatment of isocyanate residues obtained as residual substances in production of isocyanates which are raw materials for polyurethane or the like.

In addition, the method for treating carbonates according to the present invention can be used for treatment of carbonates such as dialkyl carbonate, diaryl carbonate, or alkyl aryl carbonate.

The invention claimed is:

1. A method for treating isocyanate residues, comprising:
blending carbonate with the isocyanate residues which are obtained by separating isocyanate and alcohol from a decomposition solution resulting from thermal decomposition reaction of carbamate produced by reaction of raw material amine, urea and/or N-unsubstituted carbamic acid ester, and alcohol, and
decomposing the isocyanate residues blended with the carbonate through contact with high pressure and high temperature water having a pressure of 3 to 30 MPa and a temperature of 190 to 350°C. to obtain recovered amine and alcohol,
wherein the carbonates is obtained by further roughly separating from low-boiling components containing carbonate separated after the carbamate formation reaction.

2. The method for treating isocyanate residues according to claim 1, wherein the carbonate contains N-unsubstituted carbamic acid ester.

3. The method for treating isocyanate residues according to claim 1, wherein
the low-boiling components further contain N-unsubstituted carbamic acid ester, the carbonate as well as the N-unsubstituted carbamic acid ester is roughly separated from the low-boiling components, and the N-unsubstituted carbamic acid ester is used as a raw material component for the carbamate formation reaction.

4. A method for treating carbonates, comprising decomposing at least one carbonate selected from the group consisting of dialkyl carbonate, diaryl carbonate, and alkyl aryl carbonate into alcohol by contact with high pressure and high temperature water having a pressure of 3 to 30 MPa and a temperature of 190 to 350°C., the carbonate being obtained by carbamate formation reaction of raw material amine, urea and/or N-unsubstituted carbamic acid ester, and alcohol, wherein the carbonate is obtained by further roughly separating from low-boiling components containing N-unsubstituted carbamic acid ester and carbonate, which are separated alter the carbamate formation reaction.

5. The method for treating carbonates according to claim 4, wherein the carbonate contains N-unsubstituted carbamic acid ester.

6. The method for treating carbonates according to claim 4, wherein the alcohol obtained by decor posing the carbonate is used as a raw material component for the carbamate formation reaction.

7. The method for treating carbonates according to claim 4, wherein the N-unsubstituted carbamic acid ester is roughly separated from the low-boiling components and then used as a raw material component for the carbamate formation reaction.

* * * * *